US009421392B2

(12) United States Patent
Reihl et al.

(10) Patent No.: US 9,421,392 B2
(45) Date of Patent: *Aug. 23, 2016

(54) METHOD AND APPARATUS FOR DETERMINING THE PROXIMITY OF A TMS COIL TO A SUBJECT'S HEAD

(75) Inventors: Mark Edward Reihl, Doylestown, PA (US); Kenneth Marc Ghiron, Allentown, PA (US); Stanford W. Miller, Kennesaw, GA (US)

(73) Assignee: NEURONETICS, INC., Malvern, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/449,379

(22) Filed: Apr. 18, 2012

(65) Prior Publication Data

US 2012/0203054 A1    Aug. 9, 2012

Related U.S. Application Data

(63) Continuation of application No. 10/825,043, filed on Apr. 15, 2004, now Pat. No. 8,177,702.

(51) Int. Cl.
*A61N 2/02* (2006.01)
*A61N 2/00* (2006.01)

(52) U.S. Cl.
CPC .. *A61N 2/006* (2013.01); *A61N 2/02* (2013.01)

(58) Field of Classification Search
CPC ......... A61N 2/02; A61N 2/006; A61N 2/002; A61N 2/004; A61N 2/008; A61N 2/00; A61N 2/12; A61N 1/0484; A61N 1/08
USPC ............................ 600/9–15; 607/46; 606/130
See application file for complete search history.

(56) References Cited

U.S. PATENT DOCUMENTS 3,683,923 A    8/1972   Anderson
4,473,074 A    9/1984   Vassiliadis
(Continued)

FOREIGN PATENT DOCUMENTS

CA    2295134 A1    7/1999
EP    0998958 A2    5/2000
(Continued)

OTHER PUBLICATIONS

Awiszus et al., "Characterization of Paired-Pulse Transcranial Magnetic Stimulation Conditions Yielding Intracortical Inhibition of I-Wave Facilitation using a Threshold Paradigm", Experimental Brain Research, Nov. 1999, 129(2), 317-324.
(Continued)

*Primary Examiner* — Christine H Matthews
(74) *Attorney, Agent, or Firm* — Condo Roccia Koptiw LLP

(57) ABSTRACT

A proximity sensor for a transcranial magnetic stimulation (TMS) system detects the proximity of a TMS coil assembly to a position at which the coil is to receive pulses during TMS treatment and provides feedback to the operator so that the operator may adjust the TMS coil assembly to maintain optimal positioning during treatment. A flexible substrate containing a sensor or sensor array is disposed between the TMS coil assembly and the position such that the coupling of the TMS coil assembly to the position may be detected by the sensor(s). Sensor outputs are processed by signal processing circuitry to provide an indication of whether the TMS coil assembly is properly disposed with respect to the position during TMS treatment. A display provides an indication of how to adjust the TMS coil assembly to improve the positioning of the TMS coil assembly.

44 Claims, 17 Drawing Sheets

(56) References Cited

U.S. PATENT DOCUMENTS

| | | | |
|---|---|---|---|
| 4,638,798 A | 1/1987 | Shelden et al. | |
| 4,712,558 A | 12/1987 | Kidd et al. | |
| 4,995,395 A | 2/1991 | Ilmoniemi et al. | |
| 5,097,833 A | 3/1992 | Camposm | |
| 5,116,304 A | 5/1992 | Cadwell | |
| 5,254,123 A | 10/1993 | Bushey | |
| 5,299,569 A | 4/1994 | Wernicke et al. | |
| 5,370,117 A | 12/1994 | McLaurin, Jr. | |
| 5,655,534 A | 8/1997 | Ilmoniemi | |
| 5,707,334 A | 1/1998 | Young | |
| 5,725,471 A | 3/1998 | Davey et al. | |
| 5,769,778 A | 6/1998 | Abrams et al. | |
| 5,812,301 A | 9/1998 | Nakamura | |
| 5,813,970 A | 9/1998 | Abrams et al. | |
| 5,820,623 A | 10/1998 | Ng | |
| 5,828,770 A | 10/1998 | Leis et al. | |
| 5,855,582 A | 1/1999 | Gildenberg | |
| 5,923,417 A | 7/1999 | Leis | |
| 6,061,644 A | 5/2000 | Leis | |
| 6,066,084 A | 5/2000 | Edrich et al. | |
| 6,086,525 A | 7/2000 | Davey et al. | |
| 6,091,981 A * | 7/2000 | Cundari et al. | 600/407 |
| 6,117,066 A | 9/2000 | Abrams et al. | |
| 6,169,963 B1 | 1/2001 | Markov | |
| 6,179,771 B1 | 1/2001 | Mueller | |
| 6,198,958 B1 | 3/2001 | Ives et al. | |
| 6,210,317 B1 | 4/2001 | Bonlie | |
| 6,253,109 B1 | 6/2001 | Gielen | |
| 6,256,531 B1 | 7/2001 | Ilmoniemi et al. | |
| 6,279,579 B1 | 8/2001 | Riaziat et al. | |
| 6,288,785 B1 | 9/2001 | Frantz et al. | |
| 6,355,049 B1 | 3/2002 | Gill | |
| 6,366,814 B1 | 4/2002 | Boveja et al. | |
| 6,389,318 B1 | 5/2002 | Zarinetchi et al. | |
| 6,402,678 B1 | 6/2002 | Fischell et al. | |
| 6,418,345 B1 | 7/2002 | Tepper et al. | |
| 6,463,328 B1 | 10/2002 | John | |
| 6,480,743 B1 | 11/2002 | Kirkpatrick et al. | |
| 6,484,059 B2 | 11/2002 | Gielen | |
| 6,488,617 B1 | 12/2002 | Katz | |
| 6,497,648 B1 | 12/2002 | Rey | |
| 6,503,187 B1 | 1/2003 | Ilmoniemi et al. | |
| 6,516,213 B1 | 2/2003 | Nevo | |
| 6,516,288 B2 | 2/2003 | Bagne | |
| 6,537,197 B1 | 3/2003 | Ruohonen et al. | |
| 6,551,233 B2 | 4/2003 | Perreault et al. | |
| 6,553,326 B1 | 4/2003 | Kirsch et al. | |
| 6,560,490 B2 | 5/2003 | Grill et al. | |
| 6,567,702 B1 | 5/2003 | Nekhendzy et al. | |
| 6,571,123 B2 | 5/2003 | Ives et al. | |
| 6,572,528 B2 | 6/2003 | Rohan et al. | |
| 6,625,563 B2 | 9/2003 | Kirsch et al. | |
| 6,827,681 B2 | 12/2004 | Tanner et al. | |
| 6,849,040 B2 | 2/2005 | Ruohonen et al. | |
| 6,978,179 B1 | 12/2005 | Flagg et al. | |
| 7,367,935 B2 | 5/2008 | Mechlenburg et al. | |
| 7,651,459 B2 | 1/2010 | Cameron et al. | |
| 2001/0002441 A1 | 5/2001 | Boveja | |
| 2001/0018547 A1 | 8/2001 | Mechlenburg et al. | |
| 2002/0013612 A1 | 1/2002 | Whitehurst | |
| 2002/0087101 A1* | 7/2002 | Barrick et al. | 600/587 |
| 2002/0087201 A1 | 7/2002 | Firlik et al. | |
| 2002/0091419 A1 | 7/2002 | Firlik et al. | |
| 2002/0103515 A1 | 8/2002 | Davey et al. | |
| 2002/0160436 A1 | 10/2002 | Markov et al. | |
| 2002/0169355 A1 | 11/2002 | Rohan et al. | |
| 2003/0004392 A1 | 1/2003 | Tanner et al. | |
| 2003/0023159 A1 | 1/2003 | Tanner | |
| 2003/0028072 A1 | 2/2003 | Fischell et al. | |
| 2003/0050527 A1 | 3/2003 | Fox et al. | |
| 2003/0065243 A1 | 4/2003 | Tanner | |
| 2003/0073899 A1 | 4/2003 | Ruohonen et al. | |
| 2003/0074032 A1 | 4/2003 | Gliner | |
| 2003/0082507 A1 | 5/2003 | Stypulkowski | |
| 2003/0088274 A1 | 5/2003 | Gliner et al. | |
| 2003/0097161 A1 | 5/2003 | Firlik et al. | |
| 2003/0125786 A1 | 7/2003 | Gliner et al. | |
| 2003/0130706 A1 | 7/2003 | Sheffield et al. | |
| 2004/0010177 A1 | 1/2004 | Rohan et al. | |
| 2004/0019370 A1 | 1/2004 | Gliner et al. | |
| 2004/0039279 A1 | 2/2004 | Ruohonen | |
| 2004/0051279 A1 | 3/2004 | Grant et al. | |
| 2004/0077921 A1 | 4/2004 | Becker et al. | |
| 2004/0077923 A1 | 4/2004 | Frimerman et al. | |
| 2004/0127942 A1 | 7/2004 | Yomtov et al. | |
| 2004/0138524 A1 | 7/2004 | Ueda et al. | |
| 2004/0153129 A1 | 8/2004 | Pless et al. | |
| 2004/0167592 A1 | 8/2004 | Grove et al. | |
| 2004/0172012 A1 | 9/2004 | Otsuka et al. | |
| 2004/0193001 A1 | 9/2004 | Miller | |
| 2004/0193002 A1 | 9/2004 | Tanner et al. | |
| 2005/0021104 A1 | 1/2005 | DiLorenzo | |
| 2005/0124848 A1 | 6/2005 | Holzner | |
| 2005/0216071 A1 | 9/2005 | Devlin et al. | |
| 2005/0228209 A1 | 10/2005 | Schneider et al. | |
| 2005/0234286 A1 | 10/2005 | Riehl et al. | |
| 2005/0256539 A1 | 11/2005 | George et al. | |
| 2006/0052687 A1 | 3/2006 | Ruohonen | |
| 2012/0253098 A1 | 10/2012 | George et al. | |

FOREIGN PATENT DOCUMENTS

| | | |
|---|---|---|
| EP | 1273320 A1 | 1/2003 |
| JP | 2000-504966 A | 4/2000 |
| JP | 2003-180649 A | 7/2003 |
| JP | 2004-511314 A | 4/2004 |
| JP | 2005-528141 A | 9/2005 |
| WO | WO 98/06342 A1 | 2/1998 |
| WO | WO 99/64884 A1 | 12/1999 |
| WO | WO 00/74777 A1 | 12/2000 |
| WO | WO 01/12236 A2 | 2/2001 |
| WO | WO 01/28622 A2 | 4/2001 |
| WO | WO 01/97906 A2 | 12/2001 |
| WO | WO 02/09811 A1 | 2/2002 |
| WO | WO 02/31604 A1 | 4/2002 |
| WO | WO 02/32504 A2 | 4/2002 |
| WO | WO 02/072194 A2 | 9/2002 |
| WO | WO 02/085449 A2 | 10/2002 |
| WO | WO 02/085454 A1 | 10/2002 |
| WO | WO 02/089902 A2 | 11/2002 |
| WO | WO 02/094997 A2 | 11/2002 |
| WO | WO 03/035163 A2 | 5/2003 |
| WO | WO 03/084605 A1 | 10/2003 |
| WO | WO 03/090604 A2 | 11/2003 |
| WO | WO 03/098268 A1 | 11/2003 |
| WO | WO 2004/100765 A2 | 11/2004 |
| WO | WO 2005/000401 A1 | 1/2005 |
| WO | WO 2005/065768 A1 | 7/2005 |
| WO | WO 2005/067610 A2 | 7/2005 |

OTHER PUBLICATIONS

Baudewig et al., "Functional MRI of Cortical Activations Induced by Transcranial Magnetic Stimulation (TMS)", Brain Imaging-Neuro Report, Nov. 16, 2001, 12(16), 3543-3548.

Bohning et al., "A Combined TMS/fMRI Study of Intensity-Dependant TMS over Motor Cortex", Society of Biological Psychiatry, Feb. 15, 1999, 45(4), 385-394.

Bohning et al., "A TMS Coil Positioning/Holding System for MR Image-Guided TMSInter leaved with fMRI", Clinical Neurophysiology, Nov. 2003, 114(11), 2210-2219.

Bohning et al., "BOLD-fMRI Response to Single-Pulse Transcranial Magnetic Stimulation (TMS)", Journal of Magnetic Resonance Imaging, Jun. 2000, 11(6), 569-574.

Garcia-Toro et al., "Modest Adjunctive Benefit with Transcranial Magnetic Stimulation in Medication-Resistant Depression", Journal of Affective Disorders, May 2001, 64(2-3), 271-275.

George et al., "A Controlled Trial of Daily Left Prefrontal Cortex TMS for Treating Depression", Society of Biological Psychiatry, Nov. 15, 2000, 48(10), 962-970.

George, M. S., "New Methods of Minimally Invasive Brain Modulation as Therapies in Psychiatry: TMS, MST, VNS and DBS", Chinese Medical Journal (Taipei), Aug. 2002, 65(8), 349-360.

(56) References Cited

OTHER PUBLICATIONS

Greene, Y.M., APA Meeting, "Electromagnetic Stimulation Relieves Depression", http://HealthyPlace.com, May 17, 1999, 3 pages.
Hess et al., "Magnetic Stimulation of the Human Brain: Influence of Size and Shape of the Stimulating Coil", Motor Disturbances II, May 1990, 3, 31-42.
Iramina et al., "Effects of Transcranial Magnetic Stimulation on EEG Activity", IEEE transactions on Magnetics, Sep. 2002, 38(5), 3347-3349.
Lisanby et al., "Magnetic Seizure Therapy of Major Depression", Arch. Gen. Psychiatry, Mar. 2001, 58, 303-307.
Lisanby et al., "Safety and Feasibility of Magnetic Seizure Therapy (MST) in Major Depression: Randomized Within-Subject Comparison with Electroconvulsive Therapy", Neuropsychopharmacology, New York State Psychiatric Institute, Jul. 2003, 28(10), 1852-1865.
Lisanby et al., "Sham TMS: Intracerebral Measurement of the Induced Electrical Field and the Induction of Motor-Evoked Potentials", Society of Biological Psychiatry, Mar. 1, 2001, 49(5), 460-463.
Lisanby, S. H., "Update on Magnetic Seizure Therapy: A Novel Form of Convulsive Therapy", The Journal of ECT, Dec. 2002, 18(4), 182-188.
Loo et al., "Transcranial Magnetic Stimulation (TMS) in Controlled Treatment Studies: Are Some "Sham" Forms Active?", Society of Biological Psychiatry, Feb. 15, 2000, 47(4), 325-331.
Nahas et al., "Left Prefrontal Transcranial Magnetic Stimulation (TMS) Treatment of Depression in Bipolar Affective Disorder: A Pilot Study of Acute Safety and Efficacy", Bipolar Disorders, Feb. 2003, 5(1), 40-47.
Nahas et al., "Safety and Feasibility of Repetitive Transcranial Magnetic Stimulation in the Treatment of Anxious Depression in Pregnancy: A Case Report", J. Clin. Psychiatry, Jan. 1999, 60, 50-52.
Nahas et al., "Unilateral Left Prefrontal Transcranial Magnetic Stimulation (TMS) Produces Intensity-Dependent Bilateral Effects as Measured by Interleaved Bold fMRI", Society of Biological Psychiatry, Nov. 1, 2001, 50(9), 712-720.
Pascual-Leone et al., "Rapid-Rate Transcranial Magnetic Stimulation of Left Dorsolateral Prefrontal Cortex in Drug-Resistant Depression", The Lancet, Jul. 27, 1996, 348(9022), 233-237.
Pridmore, S., "Rapid Transcranial Magnetic Stimulation and Normalization of the Dexamethasone Suppression Test", Psychiatry and Clinical Neurosciences, Feb. 1999, 53(1), 33-37.
Roth et al., "A Coil Design for Transcranial Magnetic Stimulation of Deep Brain Regions", Journal of Clinical Neurophysiology, Aug. 2002, 19(4), 361-370.
Ruohonen, J., "Electroencephalography Combined with TMS", BioMag Laboratory, Helsinki University Central Hospital, http://www.biomag.helsinki.fi/tms/TMSEEG.html, Oct. 6, 1999, 22 pages.
Sommer et al., "Increased Transcranial Magnetic Motor Threshold after ECT", European Archives of Psychiatry and Clinical Neuroscience, Oct. 2002, 252(5), 250-252.
Terrace et al., "The Cognitive Effects of Electroconvulsive Shock and Magnetic SeizureTherapy in Rhesus Monkeys", Society for Neuroscience Abstract Viewer and Itinerary Planner, Dec. 2002, Abstract Only # 536.7, 27(1), 1418.
Trivedi, M. H., "Treatment-Resistant Depression: New Therapies on the Horizon", Annals of Clinical Psychiatry, Mar. 2003, 15(1), 59-70.
Wassermann, E. M., "Repetitive Transcranial Magnetic Stimulation: An Introduction and Overview", CNS Spectrums, The International Journal of Neuropsychiatric Medicine, Jan. 1997, 7 pages.
Grafman, J., "TMS as a Primary Brain Mapping Tool", Transcranial Magnetic Stimulation in Neuropsychiatry, First Edition, American Psychiatric Press, 2000, 115-140.
Lorberbaum, J. P., "Safety Concerns of TMS", Transcranial Magnetic Stimulation in Neuropsychiatry, First Edition, American Psychiatric Press, 2000, 141-161.

* cited by examiner

Display indicating poor contact with scalp

Display indicating good contact with scalp

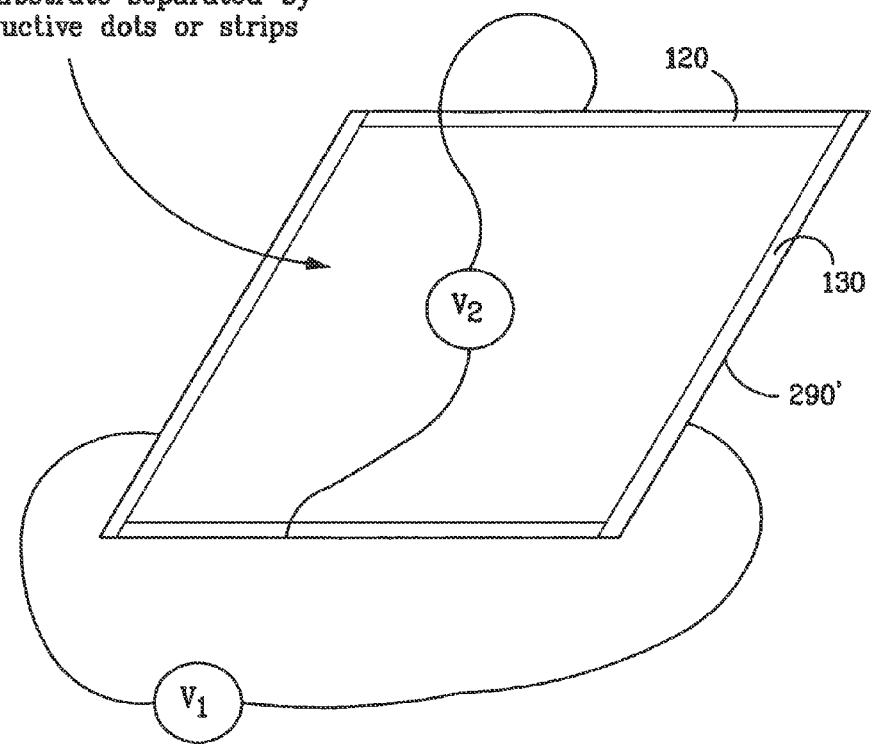

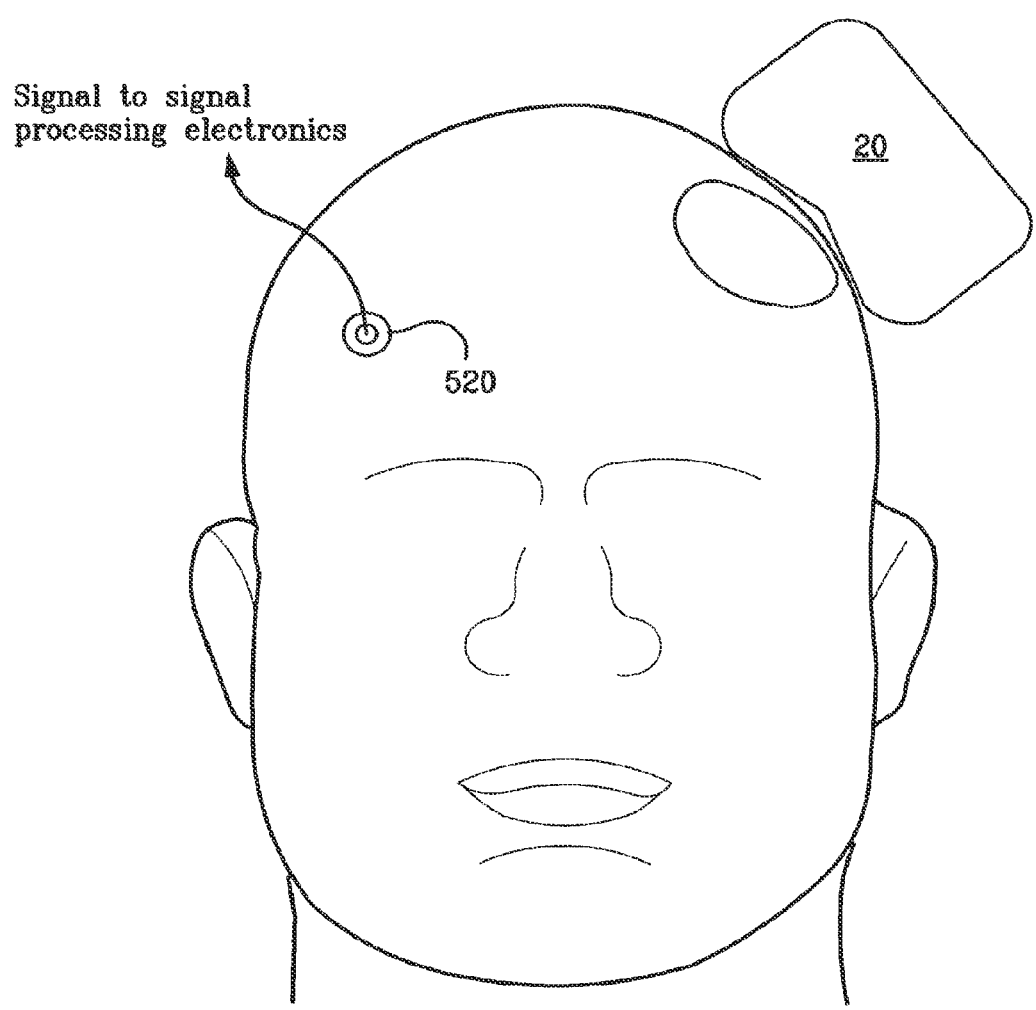

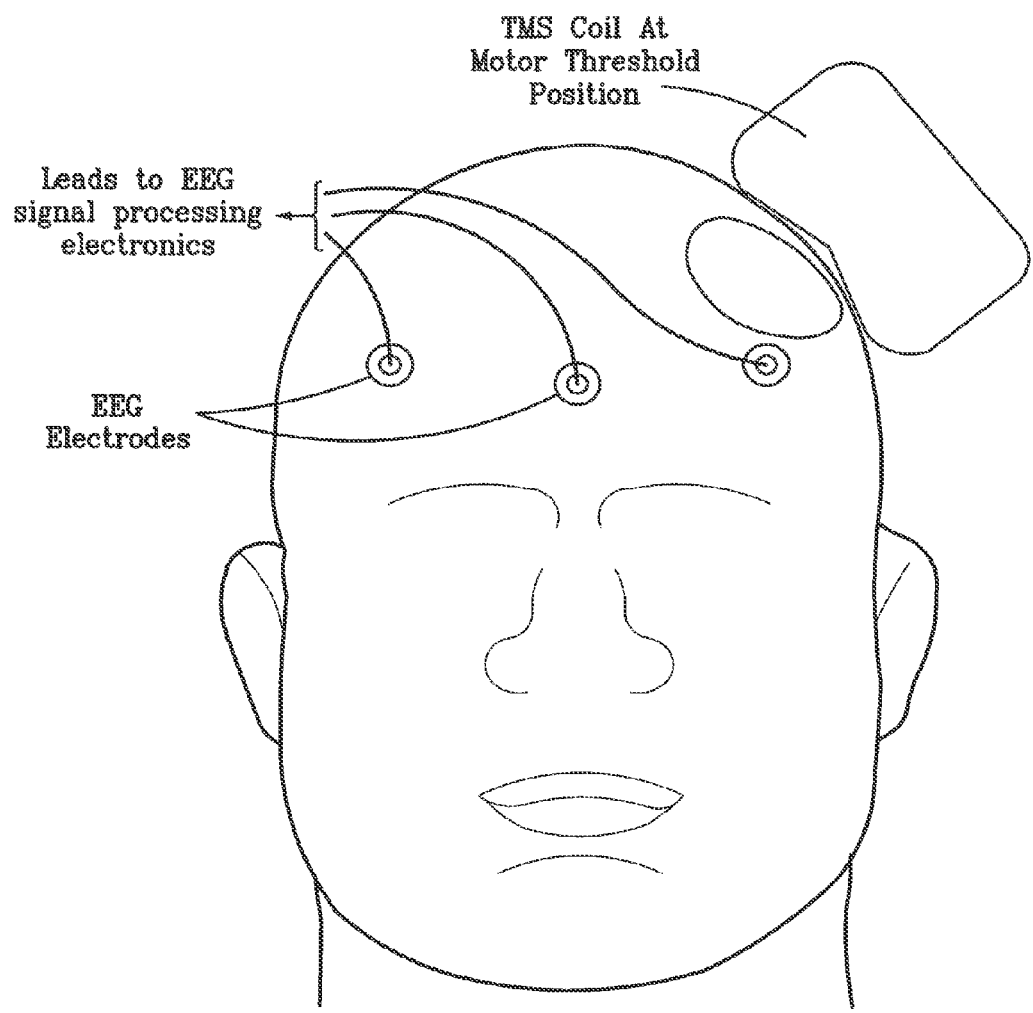

METHOD AND APPARATUS FOR DETERMINING THE PROXIMITY OF A TMS COIL TO A SUBJECT'S HEAD

CROSS REFERENCE TO RELATED APPLICATION

This application claims the benefit of U.S. application Ser. No. 10/825,043 filed on Apr. 15, 2004, now U.S. Pat. No. 8,177,702, issued May 15, 2012, which is incorporated herein by reference as if fully set forth.

FIELD OF THE INVENTION

The present invention relates to a method and apparatus for determining the proximity of a TMS treatment coil to a position on a patient and, more particularly, to a proximity measurement and contact positioning apparatus and method for determining whether a TMS coil is properly seated against a patient's head during treatment.

BACKGROUND OF THE INVENTION

Current methods of placement and positioning of coils for Transcranial Magnetic Stimulation (TMS) studies are either manual methods or approaches designed for research that require expensive and complex imaging or computational systems to determine three dimensional spatial coordinates for positioning reference. These techniques have severe clinical limitations. The manual methods do not provide a convenient means for repeated and accurate placement, while the three dimensional spatial methods based on imaging modalities are expensive, time consuming, and not conducive to clinical use. Accordingly, the present assignee has developed a positioning technique for clinical use that provides a simple way for the operator to perform repeated and accurate coil placement for TMS studies and treatments in a time-efficient and inexpensive manner. This TMS coil positioning technique is described in U.S. patent application Ser. No. 10/752,164, filed on Jan. 6, 2004, the contents of which are incorporated herein by reference.

Further techniques are also needed to comfortably hold the coil in place at the treatment position throughout a therapy session. Close approximation of the TMS stimulation coil to the patient's head during location of the motor threshold position or during therapy applications is critical to ensure that the proper magnetic field intensity is applied to the patient. The coil must remain in contact with the scalp throughout the application of stimulation pulses. The clinician does not currently have a good method to ensure that the coil is in contact, and has no means of feedback as to whether the coil has moved away from the scalp during treatment. If the coil movement occurs during the motor threshold (MT) level determination procedure, an inappropriately high power setting may be used. On the other hand, if the movement occurs after MT determination and during the treatment session, an inappropriately low magnetic field may be applied to the patient resulting in possibly reduced efficacy.

Current methods of holding the TMS coil against the patient's head include holding it by hand throughout the TMS procedure, supporting it with a mechanical arm and relying on the patient to remain still relative to the coil throughout the procedure, and mechanical alignment methods (e.g. Brainsight™ system) that physically restrain the patient's head against the coil. However, such solutions do not ensure that the coil is initially positioned against the patient's head or that the coil stays against the head throughout the procedure. These methods rely on the clinician to visually observe that contact is being made. Such observations may not be reliably be made continuously throughout the procedure. In addition, there are no solutions that provide feedback to the operator as to the state of coil contact.

Many companies provide pressure and contact sensors, including for medical applications (e.g. Tekscan), but these sensors are not designed for optimal use in the unique environment of a pulsed high magnetic field or for TMS use, and the present inventors are not aware that such sensors have been used to assist the clinician in maintaining TMS coil contact with a subject's head throughout treatment. Accordingly, an apparatus and technique for detecting that a TMS coil is and remains in contact with the patient throughout the TMS therapy procedure is needed. The present invention addresses this need in the art.

SUMMARY OF THE INVENTION

The present invention addresses the above-mentioned needs in the art by providing a transcranial magnetic stimulation (TMS) system having a TMS coil assembly, a pulse generating device that applies pulses to the TMS coil assembly during TMS treatment of a patient, a sensor disposed between the TMS coil assembly and the position at which pulses are applied (e.g., motor threshold or TMS treatment position) that detects proximity of the TMS coil assembly to the position, and signal processing circuitry that processes outputs of the sensor to provide an indication of whether the TMS coil assembly is properly disposed with respect to the position during application of pulses to the TMS coil assembly. The indication is preferably provided to a display device that indicates to an operator of the TMS device whether the TMS coil assembly is properly positioned at the position and/or in which direction to move the TMS coil assembly to the position in the event that the TMS coil assembly is not at the position. The indication also may be provided to a sound generator that generates a sound that is detected to indicate to an operator of the TMS device whether the TMS coil assembly is properly positioned at the position.

The sensor comprises a plurality of sensors, such as a sensor array, that may be disposed in or on a flexible substrate that is, in turn, placed between the TMS coil assembly and the position to determine if the TMS coil assembly is properly positioned with respect to the position during TMS therapy.

In a first embodiment, the sensors may comprise membrane switches that change state when depressed. The membrane switches may, in turn, include resistive strips that provide an output voltage that varies with position of contact on the membrane switches. The membrane switches also may include an array of separators between respective conductive films so as to form a touch screen.

In a second embodiment, the sensors may comprise variable resistance sensors that provide an output signal that is proportionate to applied contact pressure, whereby a change in resistance above a predetermined threshold is identified as an indication of contact.

In a third embodiment, the sensors may comprise one or more fluid displacement sensors and fluid filled bladders connected by a non-compressible manifold to the fluid displacement sensors such that compression of a bladder causes a change in pressure at the fluid displacement sensor. Preferably, the fluid filled bladders are disposed directly over respective pole faces of a TMS coil of the TMS coil assembly and fluid in the fluid filled bladders is a substantially non-electrically-conductive fluid so as not to interfere with the TMS field.

In a fourth embodiment, the sensors may comprise optical fibers that cross the position and an optical grating disposed on the substrate, whereby light passing through the optical fibers is deflected when contact is made by the TMS coil assembly to the position so as to change an amount of light reflected by the optical grating. The reflected light is detected by an optical detector.

In a fifth embodiment, the sensors may comprise an acoustic device that produces an acoustic sound (that may or may not be in the human audible range) when a TMS coil of the TMS coil assembly is pulsed and reduces an amplitude of the sound as the acoustic device is compressed by the TMS coil assembly against the position. Acoustic sensors detect the sound and provide a proportionate voltage signal to the signal processing circuitry for a determination as to whether an amplitude change has occurred. Acoustic sensors are not necessary if a conductive disk is configured to "rattle" in a cavity when a magnetic field is applied but is inhibited from "rattling" when the sensor is compressed against the patient.

In a sixth embodiment, the sensors may comprise inductive coupling sensors including at least one tuned coil mounted at the position on the patient. A tuned frequency of the tuned coil is selected to shift when the TMS coil assembly is in physical contact with the position. A shape of the tuned coil may be distorted when compressed against the position by the TMS coil assembly such that the resulting induced current in the tuned coil may be detected by the signal processing circuitry to provide the indication of whether the TMS coil assembly is in contact with the patient at the position.

In a seventh embodiment, the sensors may comprise EEG leads that sense currents induced in the position by a TMS pulse from the TMS coil assembly. In this embodiment, the signal processing circuitry compares amplitudes of sensed currents to a threshold to obtain an indication of whether the TMS coil assembly is properly disposed with respect to the position during TMS treatment.

In an eighth embodiment, the sensors may comprise temperature sensors. In this embodiment, the signal processing circuitry processes outputs of the temperature sensors to determine if a temperature difference between respective temperature sensors is above a predetermined threshold of if the measured temperature of one or more of the temperature sensors unexpectedly changes significantly. The predetermined threshold is set such that movement of a temperature sensor from against the head to away from the head, for example, causes a temperature change that is above the threshold while a change in sensed temperature when in the proper contact position does not exceed the threshold and may instead be used as a zeroed baseline temperature.

In a ninth embodiment, the sensors may comprise a loop of conducting material placed at the treatment position (e.g., affixed to the patient's scalp). When the TMS coil assembly is in proximity to the loop of conducting material, a voltage is induced therein when pulses are applied to the TMS coil assembly.

In a tenth embodiment, the sensors comprise an acoustic sensor (in or out of the audible range) that detects acoustic waves generated when a pulse is applied to the TMS coil assembly and that are mechanically coupled to the patient's skull and transmitted to the acoustic sensor. Decoupling of the TMS coil assembly from the patient's head causes changes in the acoustic waves that are detected by the acoustic sensor.

Other currently available sensor embodiments may be implemented by those skilled in the art based on the following detailed description.

BRIEF DESCRIPTION OF THE DRAWINGS

The above and other features and advantages will become apparent to those skilled in the art based on the following detailed description of the drawing figures, of which:

FIG. 9 illustrates an embodiment in which electrodes of a strip sensor are separated by an array of separators or non-conductive dots to create a touch screen sensor.

FIG. 15 illustrates an embodiment in which sound waves generated by pulsing of the TMS coil are coupled to the patient's head and transmitted through the skull to an acoustic transducer applied to the patient's head at a convenient location (typically not directly beneath the coil), whereby decoupling of the TMS coil from the patient's head changes the detected acoustic signal.

FIG. 17 illustrates an embodiment in which EEG-type leads and electrodes, or their equivalents, may be used to sense currents induced in the scalp by the TMS magnetic pulse.

DETAILED DESCRIPTION OF ILLUSTRATIVE EMBODIMENTS

Figure 1A:
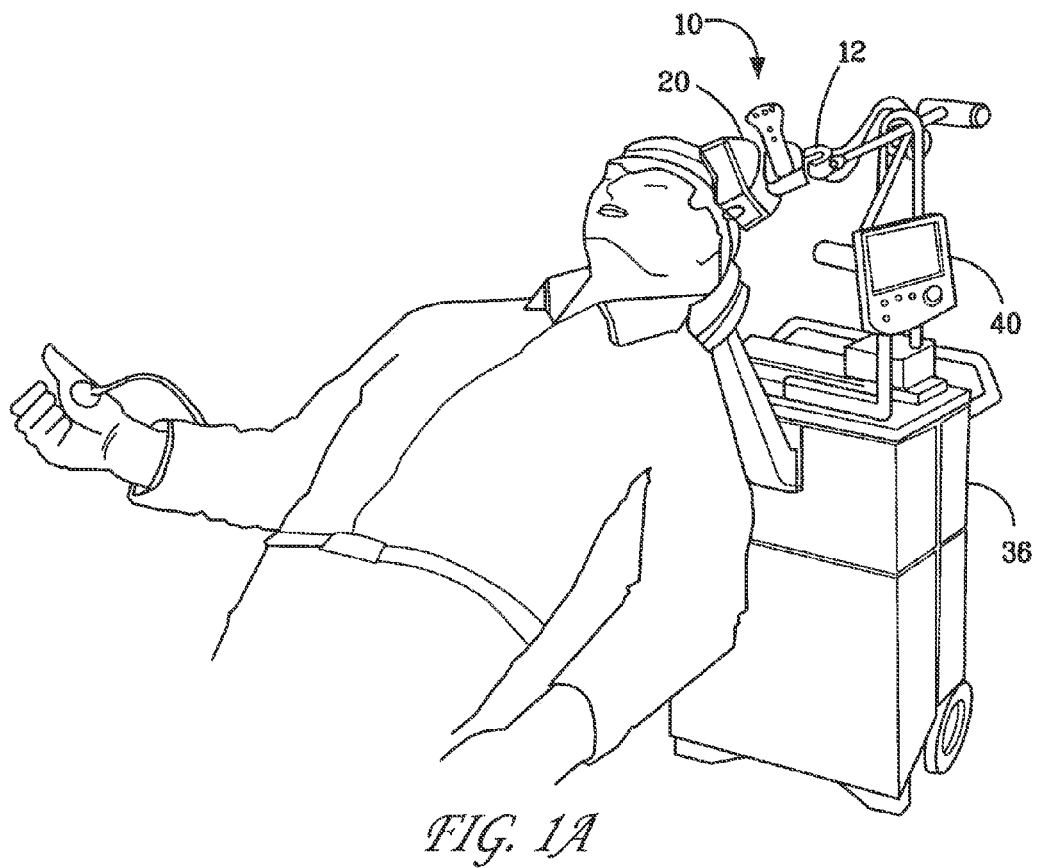
FIG. 1A illustrates a TMS system for TMS therapy using the coil position sensing system of the invention.

A detailed description of an illustrative embodiment of the present invention will now be described with reference to FIGS. 1-18. Although this description provides detailed examples of possible implementations of the present invention, it should be noted that these details are intended to be exemplary and in no way delimit the scope of the invention.

The present invention is designed to sense the positioning of a TMS coil used for treatment of central nervous system disease states using TMS therapies. While an exemplary embodiment of the invention is described with respect to the excitatory stimulation of the left prefrontal cortex for the treatment of depression, those skilled in the art will appreciate that the apparatus and techniques of the invention may be used to apply TMS therapies to many other central nervous system targets for the treatment of numerous other central nervous system diseases. For example, the TMS coil position sensing device of the invention may be used to sense the positioning of the TMS coil over the right prefrontal cortex of a patient for low frequency inhibitory stimulation in the treatment of depression. Those skilled in the art will further appreciate that the TMS coil position sensing device of the invention also may be used to sense the positioning of a TMS coil for the treatment of: epilepsy (above seizure locus), schizophrenia (at Wernicke's Area), Parkinson's Disease, Tourette's Syndrome, Amyotrophic Lateral Sclerosis (ALS), Multiple Sclerosis (MS), Alzheimer's Disease, Attention Deficit/Hyperactivity Disorder, obesity, bipolar disorder/mania, anxiety disorders (panic disorder with and without agoraphobia, social phobia a.k.a. Social Anxiety Disorder, Acute Stress Disorder, Generalized Anxiety Disorder), Post-traumatic Stress Disorder (one of the anxiety disorders in DSM), obsessive compulsive disorder (one of the anxiety disorders in DSM), pain (migraine, trigeminal neuralgia), chronic pain disorders (including neuropathic pain such as pain due to diabetic neuropathy, post-herpetic neuralgia, and idiopathic pain disorders such as fibromyalgia and regional myofascial pain syndromes), rehabilitation following stroke (neuro plasticity induction), tinnitus, stimulation of implanted neurons to facilitate integration, substance-related disorders (dependence and abuse and withdrawal diagnoses for alcohol, cocaine, amphetamine, caffeine, nicotine, cannabis), spinal cord injury and regeneration/rehabilitation, head injury, sleep deprivation reversal, primary sleep disorders (primary insomnia, primary hypersomnia, circadian rhythm sleep disorder), cognitive enhancements, dementias, premenstrual dysphoric disorder (PMS), drug delivery systems (changing the cell membrane permeability to a drug), induction of protein synthesis (induction of transcription and translation), stuttering, aphasia, dysphagia, essential tremor, Magnetic Seizure Therapy (MST), and other central nervous system disorders that may treated by the application of a magnetic field at particular locations in the brain. Of course, in each case, the treatment positions may vary; however, in each case the position sensing device of the invention is useful in maintaining the TMS coil at the treatment position during therapy.

Overview

FIG. 1A illustrates a system 10 for TMS therapy in accordance with the invention. As illustrated, a patient is placed in a comfortable reclining position with respect to the system 10. An articulating arm 12 allows the operator to adjust the TMS coil assembly 20 so that the TMS coil assembly 20 rests against the patient's head at the appropriate position (e.g., motor threshold or TMS treatment positions). During treatment, pulses are generated by pulse generating apparatus (not shown) in casing 30 and applied to TMS coil assembly 20 for generation of a magnetic field at the position. A display 40 permits the operator to interface with the pulse generating apparatus and to monitor the positioning of the TMS coil assembly 20 with respect to the position as will be described in more detail below.

Figure 1B:
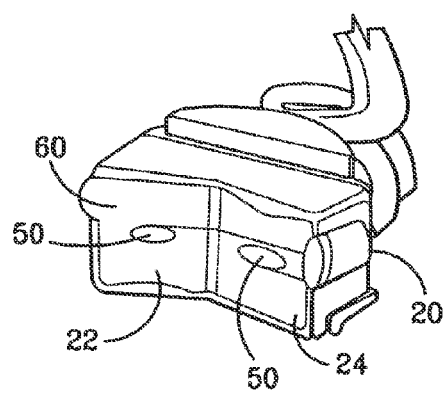
FIG. 1B illustrates the attachment of a flexible circuit substrate containing proximity sensors to the respective coil faces of the TMS coil assembly for detecting the proximity of the TMS coil to the position at which pulses are to be supplied by the TMS coil assembly in accordance with the invention.

In accordance with the present invention, pressure and/or contact sensors 50 are placed on a circuit substrate 60 that is, in turn, placed by the clinical operator between the contact surfaces of the TMS coil assembly 20 and the patient's head. Preferably, the circuit substrate 60 is flexible and disposable; however, the sensors need not be disposable or separate from the TMS coil assembly 20. As illustrated in FIG. 1B, the flexible circuit substrate 60 may be attached to respective coil treatment faces 22 and 24 of the TMS coil assembly 20 mechanically or with temporary adhesive. The sensors 50 provide output signals (analog, digital or optical) to signal processing electronics and further to an analytical processor that assesses the validity of the signal before passing the signal to a user interface that provides feedback to the operator (graphic, indicator lamp, or audible) on, for example, display 40 that contact is either proper or improper. Additionally, the operator may be provided with guidance on, for example, display 40 as to where and how to move the TMS coil assembly 20 to achieve proper contact (e.g. tilt up or down, rotate left or right, etc.). There are many suitable sensing technologies that may be used for the detection of contact as will be explained below with respect to the exemplary embodiments.

System Functionality

Figure 2:
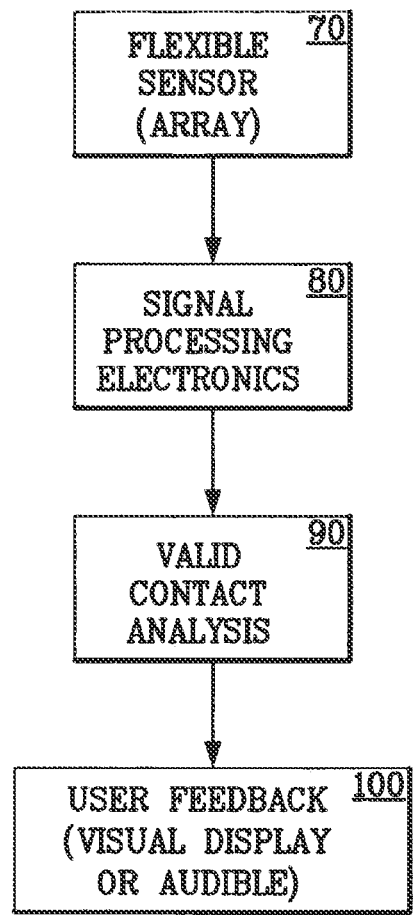
FIG. 2 illustrates a general overview of the signal processing electronics for TMS coil proximity sensing in accordance with the invention.

As illustrated in FIG. 2, the outputs of a flexible sensor or sensor array 70 of sensors 50 that has been placed on the coil treatment faces 22, 24 of the TMS coil assembly 20 so as to be adjacent the patient's head when the TMS coil assembly 20 is in the desired position are processed by signal processing electronics 80 to provide appropriate filtering and the like. The signal processing electronics is dependent upon the specific type of sensor technology used but typically includes an analog signal preamplifier followed by appropriate filtering and gain adjustment. For optical implementations, some of the processing may be done optically (e.g. filtering, polarization, wavelength separation). The processed outputs are provided by signal processing electronics 80 to valid contact analysis circuit 90 to determine whether the contact with the patient is proper (e.g., the signal is compared to thresholds). The validation of proper contact is performed by either analog or digital circuitry, or by software. These analytical algorithms depend on the nature of the artifact inherent with each type of sensor and the physical arrangement on the flexible substrate 60. The output of circuit 90 is then fed back to the user for display, for example, on display device 40. User feedback 100 may be audible, graphical, numeric, or a "go-no go" indicator. Graphic feedback may include a display of areas of physical contact, bar graphs indicating pressure levels at the critical areas, or pressure maps. The latter would require an array of sensors 70 on the sensing substrate 60 to produce a map of the type shown by way of example in FIGS. 3A and 3B, where FIG. 3A indicates poor contact with the patient's scalp and FIG. 3B indicates good contact with the patient's scalp. As illustrated, this display may be useful in guiding the operator to reposition the TMS coil assembly 20 to improve scalp contact. Audible feedback to the operator also may be provided.

Figure 3A:
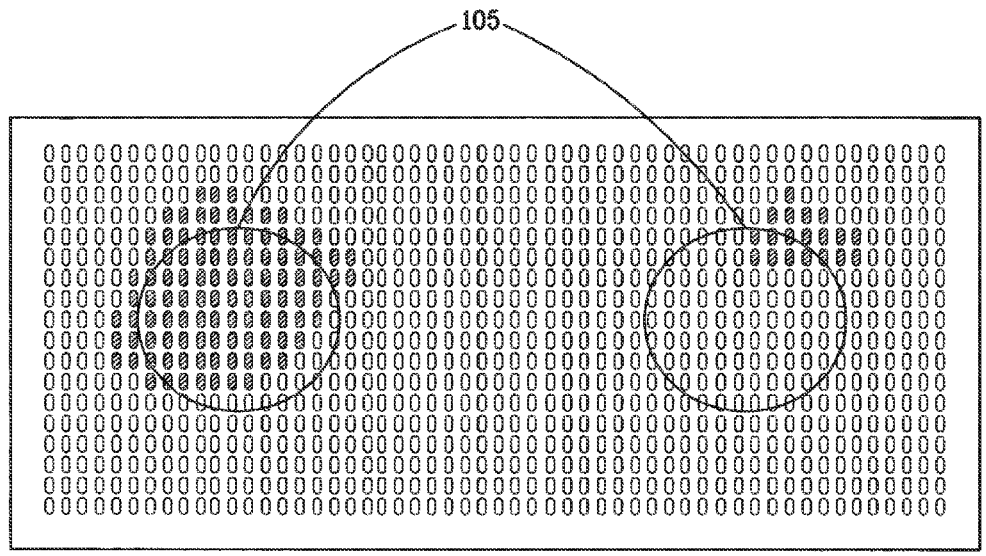
FIG. 3A illustrates a sample operator display indicating poor contact with the patient's scalp.
Figure 3B:
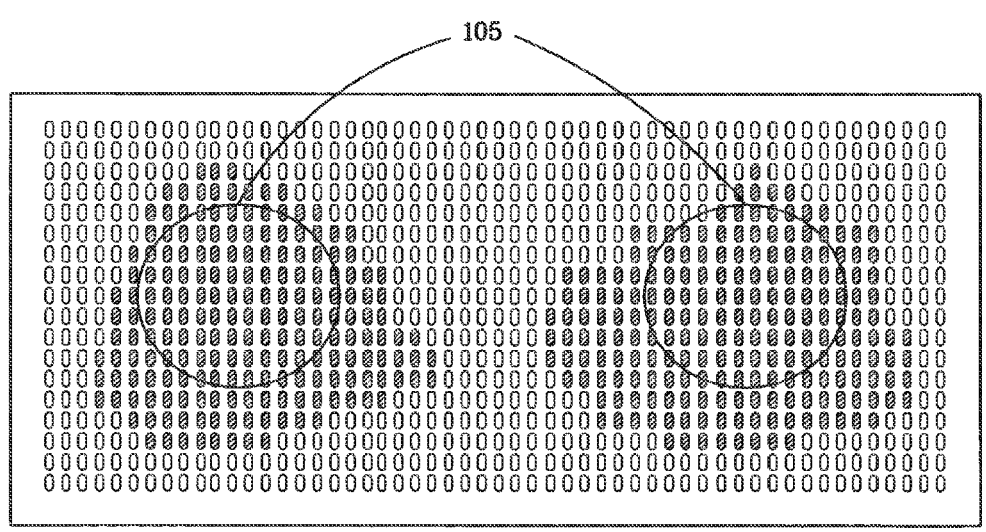
FIG. 3B illustrates a sample operator display indicating good contact with the patient's scalp.

FIGS. 3A and 3B illustrate a presently preferred embodiment in which the display 40 comprises a color LCD screen (or equivalent) of a grid map of the contact pressure across the coil pole treatment faces 22, 24. This is achieved by mapping the signals from the array of sensors 70 to the display grid of the display 40 with compressed sensors displayed in one color (e.g. green-light gray) and non-compressed sensors in another color (e.g. red-dark gray). In FIGS. 3A and 3B, the black circles 105 indicate the critical areas beneath the coil pole treatment faces 22, 24 where good contact is desired. Ideally, all the indicators within these circles should be green/light gray representing a full contact status. Analysis software also may be employed to warn the operator if any red/dark gray pixels appear in the circles 105, so that repositioning can be done and the TMS procedure continued.

Sensing Technology Options

Many different sensor technologies may be used in accordance with the invention. Presently preferred embodiments and possible implementations are described in more detail below. These embodiments are not intended to be all-inclusive. Those skilled in the art will appreciate that other comparable commercially available technologies may be used as well as future improvements to such sensing technologies as they become available.

Membrane Switches

Figure 4A:
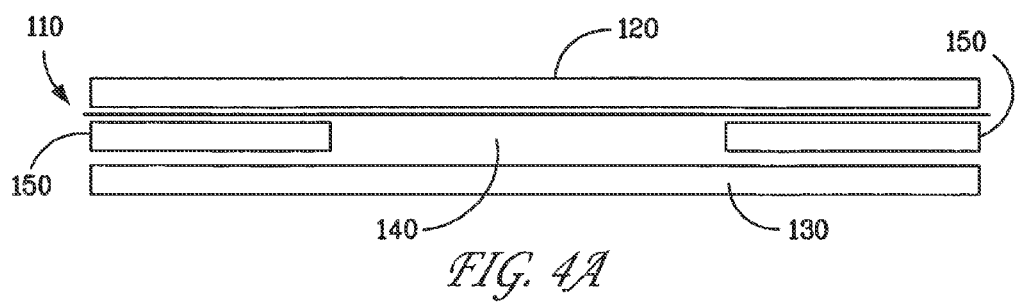
FIGS. 4A and 4B illustrate membrane switches in the no contact (FIG. 4A) and contact (FIG. 4B) positions for use as proximity sensors in accordance with the invention.
Figure 4B:
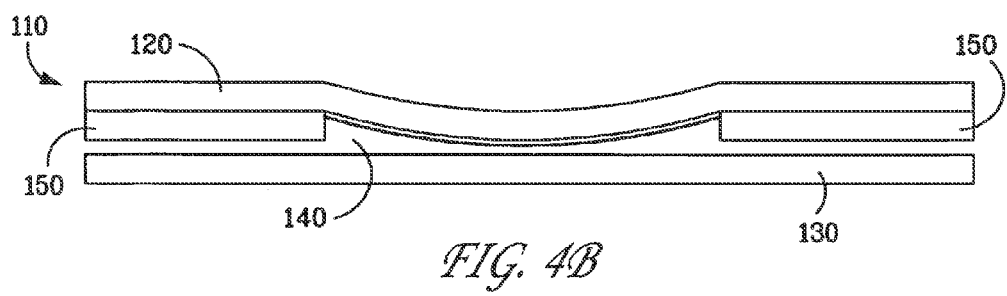

As illustrated in FIGS. 4A and 4B, membrane switches 110 are formed by mounting two conducting films or membranes 120, 130 in a parallel arrangement and separating the membranes 120, 130 by a gap 140 formed by a third, intermediate layer 150. The gap 140 is filled with a dielectric material such as air, a resistive fluid, or a gel. As illustrated in FIG. 4B, pressure applied to the membrane switches 110 causes the layers to approximate and contact each other. When the two conductive layers 120, 130 touch, electrical contact is made which is sensed as described below. The size and thickness of each sensor is selected to optimize sensitivity.

Figure 4C:
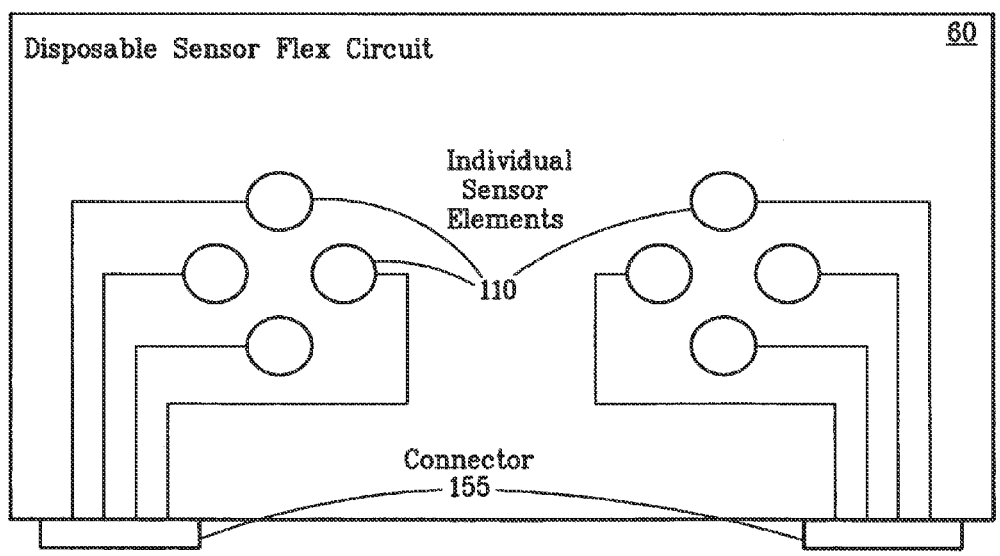
FIG. 4C illustrates an array of membrane switches fabricated on a flexible substrate for application to the face of the TMS coil assembly in accordance with the invention.

For TMS applications, an array of such switches 110 is fabricated on a flexible substrate 60 such as that illustrated in FIG. 4C that is applied to the coil pole treatment faces 22, 24 of the TMS coil assembly 20. The switches 110 are carefully positioned on this substrate 60 so that they will detect that the patient's head is completely contacting the surface of the TMS coil of the TMS coil assembly 20 near the centers of the coil pole treatment faces 22, 24 as shown. For example, an array of four or eight switches 110 can be placed in the area of each coil pole treatment face 22, 24 as illustrated in FIG. 4C and the outputs provided to connectors 155 for provision to the signal processing electronics 80. This arrangement helps in detecting partial contact by being mapped to a graphical display on display 40 to aid the operator in positioning the TMS coil assembly 20. The use of a single switch 110 at each coil pole treatment face 22, 24 does not provide the information needed to assist the operator in positioning the coil. Instead, only a "go-no go" signal is provided. While this is useful, an output that facilitates repositioning (i.e. indicating which direction to move the coil to achieve proper contact) is preferred. Accordingly, it is desired to use multiple switches 110 to cover the treatment area. Conductive films 120, 130 of sufficient resistance should be used to reduce eddy currents and to accelerate their decay. Additionally, the conductive films 120, 130 should be patterned to reduce the flow of eddy currents using techniques known to those skilled in the art.

Figure 5:
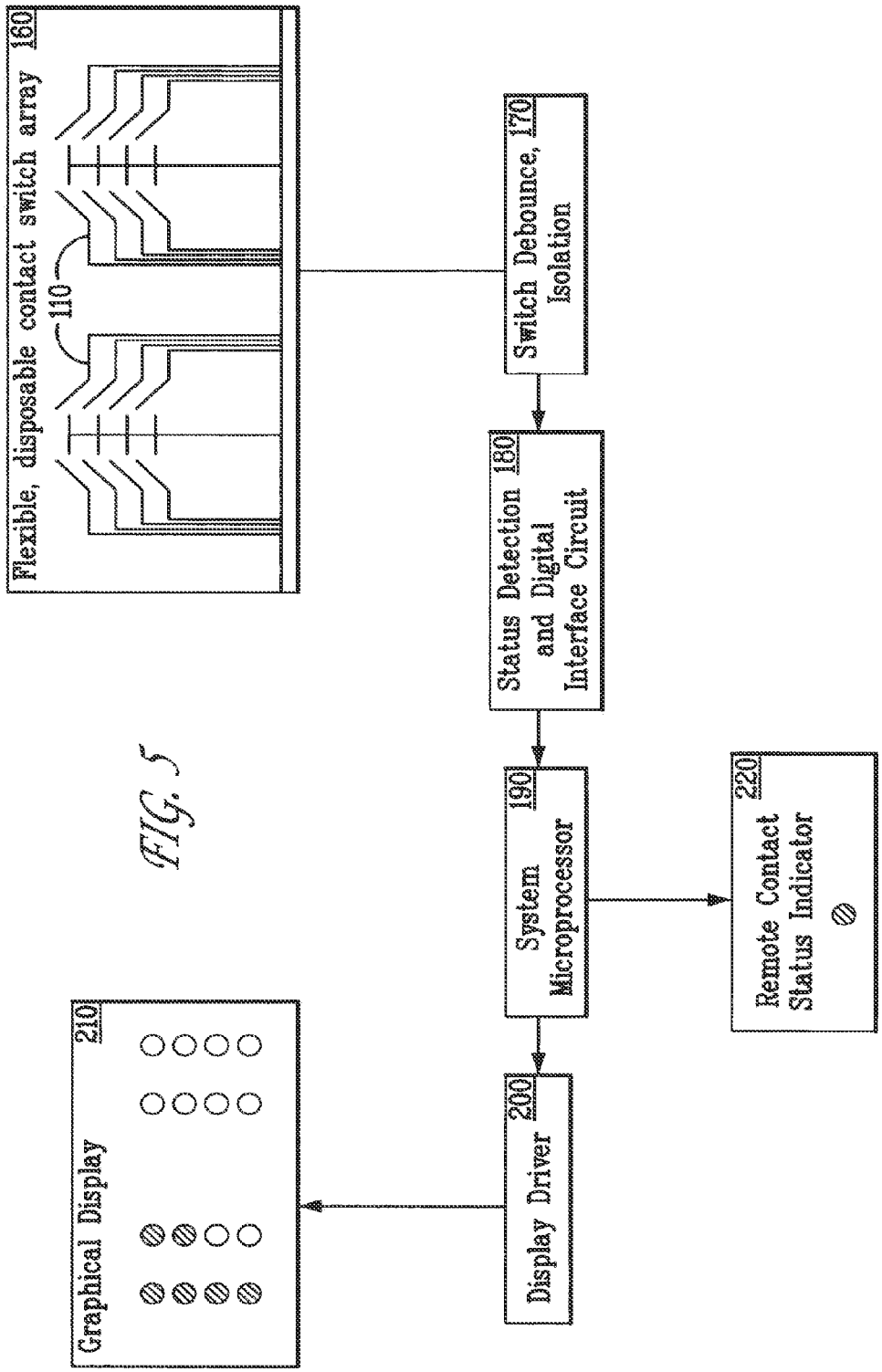
FIG. 5 illustrates a system configuration employing an array of membrane switches in accordance with the invention.

A system configuration employing an array 160 of membrane switches 110 is shown in FIG. 5. In this configuration, the array 160 of membrane switches 110 provides outputs that are debounced and isolated by a conventional debounce circuit 170 and provided to a status detection and digital interface circuit 180 to remove detection artifacts before being provided to a computer processor 190 that is used to acquire a set of digital signals that have been processed from the membrane switch array 160. Contact detection is accomplished by applying a voltage across the upper and lower membranes 120, 130 of each switch 110 of the switch array 160. When contact is achieved, current flows and is detected by a current sensing circuit within status detection and digital interface circuit 180. Typically, the signal is first debounced by debounce circuit 170, and if contact is maintained for a specified period of time (e.g. 50 milliseconds), it is assumed to be a valid contact. This status is then communicated by circuit 180 to the processor 190. Due to the unique pulsed magnetic field in the proximity of the switches, the detected signal should be filtered or gated by signal detection and digital interface circuit 180 to avoid detection artifacts. The processed output of microprocessor 190 may be provided to display driver 200 for driving graphical display 210 which may be, for example, on display 40. A remote contact status indicator 220 may also be used to indicate the state of contact (on or off).

Figure 6A:
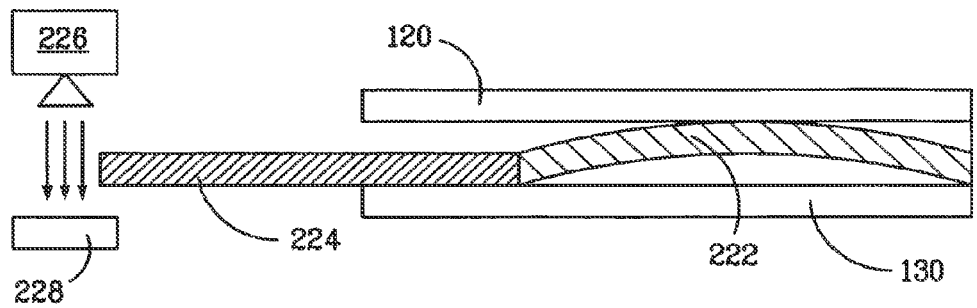
FIGS. 6A and 6B illustrate a sample micro slide embodiment in which a pre-bent actuator arm causes an opaque sliding arm to slide between a light source and an optical detector when depressed.
Figure 6B:
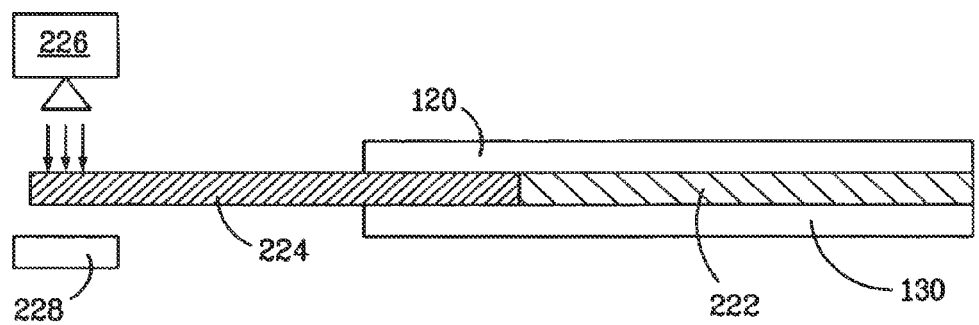

One skilled in the art would further appreciate that micro slides could be constructed of non-conductive material (e.g. plastic) and applied to the substrate 60 including the membrane switch array 160. This slide arrangement provides two functions: amplification of the compression due to contact, and allowing remote location of a motion sensor away from the critical area near the coil poles. There are a number of mechanical arrangements that can achieve this. FIGS. 6A and 6B illustrate a sample micro slide embodiment in which a pre-bent actuator arm 222 causes an opaque sliding arm 224 to slide between a light source 226 and an optical detector 228 when depressed. As shown in FIG. 6A, light from light source 226 is detected by optical detector 228 when the actuator arm 222 is not depressed, while, as shown in FIG. 6B, light from light source 226 is blocked by opaque sliding arm 224, and hence not detected by optical detector 228, when the actuator arm 222 is depressed into a compressed position. Thus, compression of the substrate membranes 120, 130 causes the opaque sliding arm 224 to move along the face of the substrate membranes 120, 130 in a direction along the coil pole treatment faces 22, 24. This motion can then be detected optically as indicated in FIG. 6A, or by other means known to those skilled in the art.

Variable Resistance Sensors

As known by those skilled in the art, force sensors may be fabricated using resistive pastes. Similarly, strain gauges may be manufactured by patterning a metal film to form a resistor on an elastic layer. Contact pressure distorts the resistor and the layer. This distortion causes a change in the resistance of the film resistor that is detected using a bridge circuit. A threshold resistance is selected to indicate contact. As is the case with membrane switches 110, the pulsed magnetic field in the proximity of the sensors must be considered when designing the sensor and detection circuit. High impedance designs are preferable to minimize induced current, and conductive loops are eliminated or kept very small in cross section to minimize induced eddy currents. Either of these variable resistance technologies may be fabricated into sensor arrays 160 as described above for the membrane switch case with similar functional advantages. However, signal processing, detection and signal validation are different than the membrane switch 110, otherwise the system configuration is very comparable to that shown in FIG. 5.

A variable resistance sensor provides a continuous signal (i.e. voltage) that is a proportionate to or a monotonic function of applied pressure. Signal processing by circuit 180 and microprocessor 190 in this case comprises filtering, applying a calibrated setting of gain and offset, and gating to synchronize with the magnetic pulse. A calibrated pressure value can be determined by digitizing (i.e. via A/D converter) the processed sensor signal, the digital value being sampled and sent to the processing computer 190 as shown in FIG. 5. Calibrated pressure values then could be displayed to the operator on display 40 or, alternatively, a threshold detection circuit may be used to decide if contact has been achieved.

Figure 7:
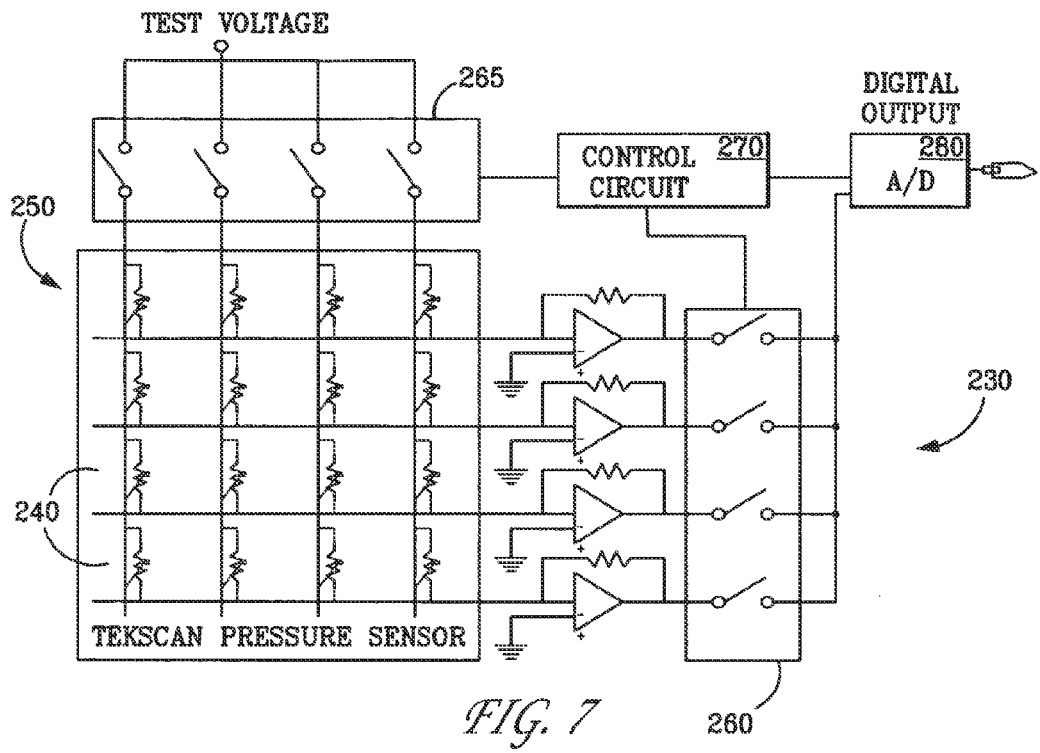
FIG. 7 illustrates a multiplexing data acquisition circuit for sampling variable resistance force sensors configured in an array in accordance with the invention.

FIG. 7 depicts a multiplexing data acquisition circuit 230 for sampling variable resistance force sensors 240 configured in an array 250. Variable resistance force sensors 240 suitable for the present application are available from Tekscan (e.g. "Flexiforce"). These sensors 240 are typically fabricated by applying a silver layer on each of two substrates. A resistive paste is placed between these silver contact areas and the assembly sealed and mechanically stabilized. The resistance between the two contacts changes with applied pressure. The contacts can be of a custom geometry and can be fabricated in large arrays. These structures lend themselves well to the desire for a low cost, flexible and disposable design. For TMS applications, single sensors 240 may be placed at each of the critical contact areas, or a number of sensors 240 may be placed at each location (e.g. FIG. 7). The advantage of employing a number of sensors 240 is that feedback can be provided to the operator as to which way to move the TMS coil assembly 20 to achieve better contact. One proposed implementation is to use a broad array or grid arrangement 250 that covers nearly the entire coil pole treatment surfaces 22, 24 of the TMs coil assembly 20. A graphic display of display 40 could then be used to guide the operator in placement. The uniqueness of this application of variable resistance sensors is the magnetic environment and the specific geometry required. The resistance of the sensors 240 must be relatively high to avoid large induced currents from the TMS pulse and the cross section of the conductive areas must be small to avoid eddy current heating.

During operation, the microprocessor 190 scans the intersecting points of the sensor's rows and columns by selectively closing switches 260, 265 under control of control circuit 270 and measures the resistance at each contact point. Each contact location is represented by a variable resistor 240 whose value is calibrated as a baseline reference when no force is applied to it. The output of this data acquisition circuit 230 is digitized by digitizer 280 and provided to microprocessor 190 where threshold detection is carried out. Microprocessor 190 then uses the pass/fail information for each sensor 240 to map the sensor states onto a graphic display of display 40. Preferably, the array-based approach is configured with a graphic display map of the sensors 240 that clearly indicate which sensors are activated (i.e. compressed) and which are not.

Other Sensors that Detect Both Position and Contact

Resistive Strip

Figure 8A:
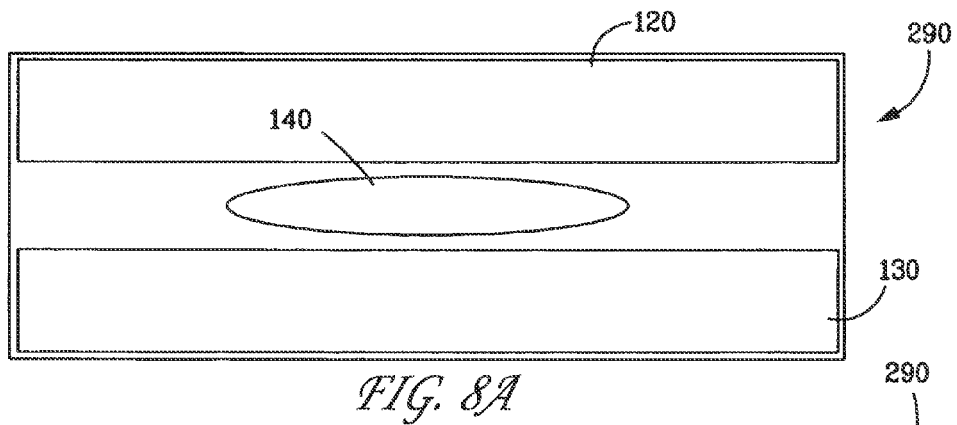
FIG. 8A illustrates a plan view of a strip sensor before compression.
Figure 8B:
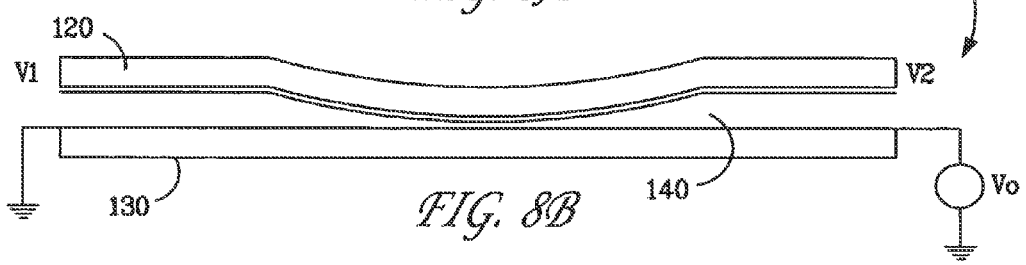
FIG. 8B illustrates a cross-section of a strip sensor after compression.

The membrane switch 110 described above can be modified to provide an output voltage that varies with position of contact. In such case, the gap area 140 is extended to form a one dimensional gap instead of a localized void. An external voltage is then applied to one of the films 120, 130, and since no current is flowing, the entire film is at equipotential. When the films 120, 130 are pressed together, the upper film 120 is brought to the same potential as the lower film 130 at the point where contact is made. The voltage V1, V2 at the ends of the upper film 120 will depend on the location and spatial extent of the contact. These voltages can be converted into a reading of the location of the pressure along the gap 140. A row of such strips can be placed in a parallel arrangement to make an area sensor 290. FIG. 8A shows a plan view of such a strip sensor 290 before compression, while FIG. 8B shows a cross-section of such a strip sensor 290 after compression, where V1 and V2 vary when the contact area is changed.

Touch Screen Technology

In a preferred embodiment illustrated in FIG. 9, touch screen technology is similar to the strip sensor 290 (FIGS. 8A and 8B) except that the electrodes 120, 130 of strip sensor 290' are separated by an array of separators or non-conductive dots or strips (not shown). This allows the contact to be sensed over an area. The position is read out by first applying a voltage $V_1$ along the horizontal direction and reading the voltage the sensor film 290' is pulled to and then applying a voltage $V_2$ along the perpendicular direction and sensing the new voltage the sensor film 290' is pulled to. One may also detect how large an area is in contact with the patient's skull by sensing the current between pairs of electrodes 120, 130 (i.e., the larger the current, the more area is in contact with the skull). Thus, the two dimensional position of the contact can be sensed. The contact position is then mapped to a graphical display on display 40 as previously described.

Pickup Loop

Figure 10:
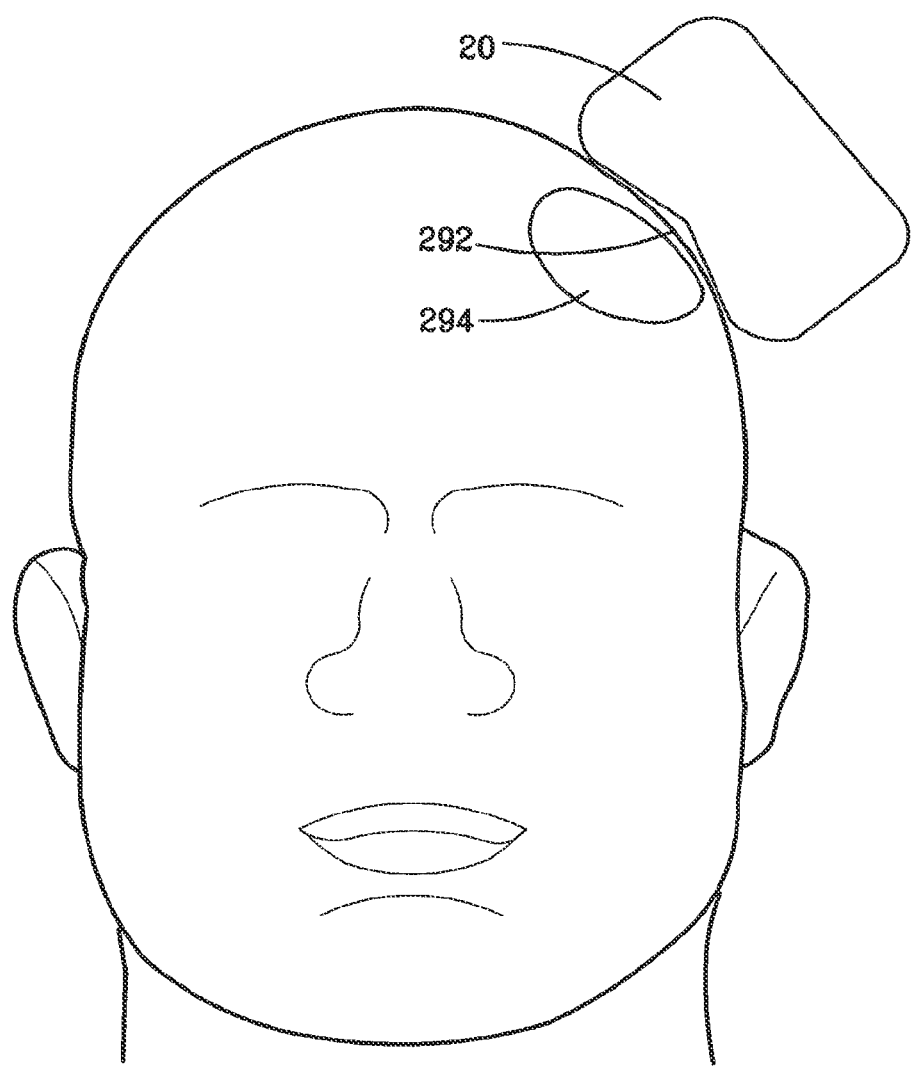
FIG. 10 illustrates an embodiment in which a loop or loops of conducting material may be affixed to the patient's head at the motor threshold (MT) position and/or the position for depression treatment.

As illustrated in FIG. 10, a loop or loops of conducting material 292 may be affixed to the patient's head at the position for the motor threshold (MT) procedure and/or a loop or loops of conducting material 294 may be affixed to the patient's head at the position for depression treatment. Then, when the TMS coil assembly 20 is placed in the proper position, a pulsed magnetic field applied by the TMS coil assembly 20 induce voltages in the loop or loops 292 or 294. If the patient moves away from the TMS coil assembly 20 during the TMS procedure, then the induced voltage in the loop or loops 292 or 294 is reduced. A threshold can be determined by the signal processing circuitry 80 for maintaining an effective treatment, and if the voltage drops below this threshold, a visible or audible signal is provided to the operator so that the TMS coil assembly 20 can be properly repositioned for the remainder of the therapy.

Fluid Displacement Sensors

Figure 11A:
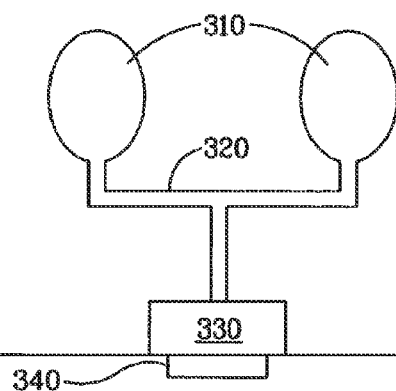
FIG. 11A illustrates fluid displacement sensors fabricated on a flexible, disposable substrate for placement on the TMS coil assembly for proximity detection in accordance with the invention.
Figure 11B:
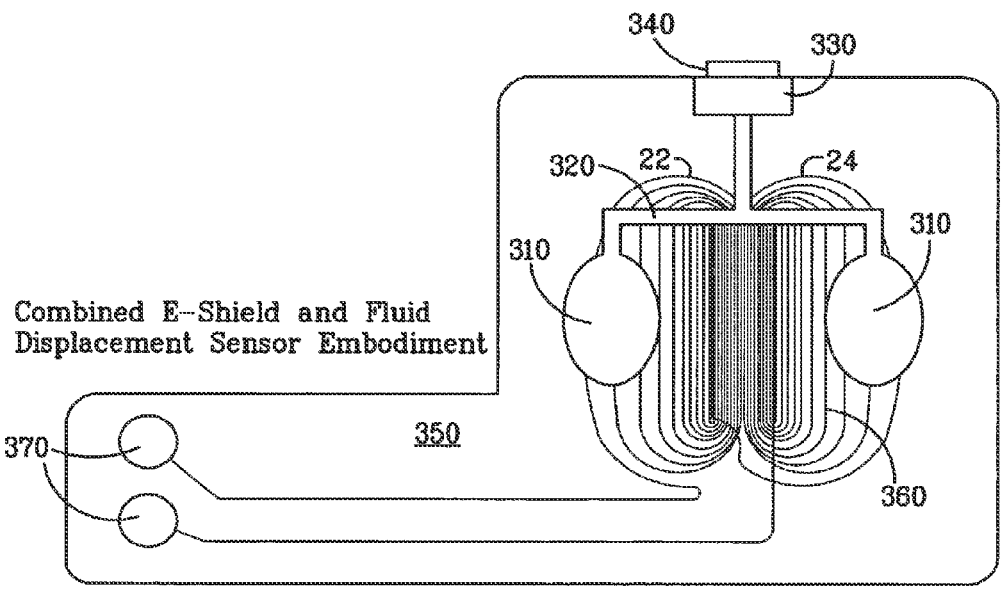
FIG. 11B illustrates the fluid displacement sensors of FIG. 11A manufactured on the same physical substrate as an e-shield device for use in TMS applications in accordance with the invention.

Fluid displacement sensors may be fabricated on a flexible, disposable substrate (e.g. polyester) 300 as illustrated in FIG. 11A. As shown, fluid filled bladders 310 are connected by a non-compressible manifold 320 such that compression of one or both of the fluid filled bladders 310 causes a change in pressure at fluid displacement sensor 330 that is detected and provided via connector 340 to the signal processing electronics 80. As illustrated in FIG. 11B, the fluid displacement sensors also may be manufactured on the same physical substrate 350 as an e-shield device. The fluid filled membrane bladders 310 are positioned directly over the coil pole treatment faces 22, 24 of coil 360 as shown and are connected to pressure transducer 330 for conversion of the fluid pressure into an analog voltage that is, in turn, connected via electrical connector 340 to signal processing circuitry 80 for the elimination of artifacts and detection of whether a threshold has been exceeded, thereby indicating proper contact on both sides of the coil 360. The fluid is high-impedance and provides for a minimal current flow and is, accordingly, substantially non-electrically-conductive so that induced eddy currents (due to the pulsing magnetic field) do not cause heating or field distortion. E-shield connectors 370 provide a mechanism for driving the e-shield coils from a remote pulse generator.

Optical Sensors

Figure 12A:
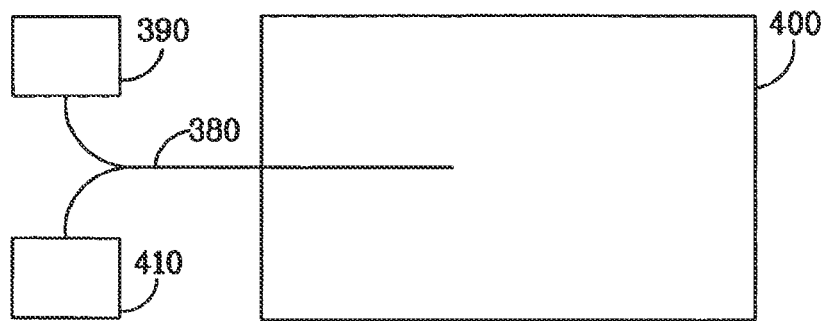
FIGS. 12A-12C illustrate an optical fiber sensor embodiment in which light is directed via an optical fiber (FIG. 12A) toward a fiber Bragg grating (FIG. 12B) where the light is deflected by fiber(s) of the fiber Bragg grating as illustrated in FIG. 12C so as to affect light transmission efficiency.
Figure 12B:
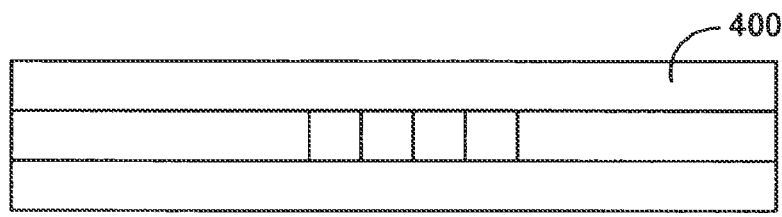
Figure 12C:
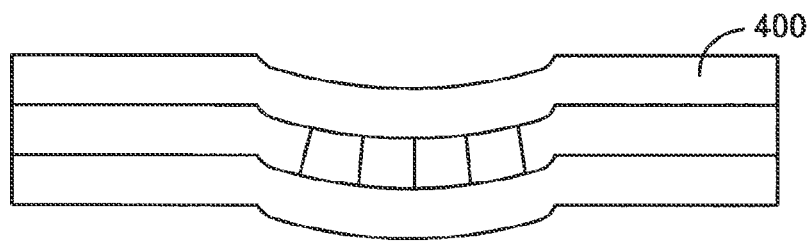
Figure 12D:
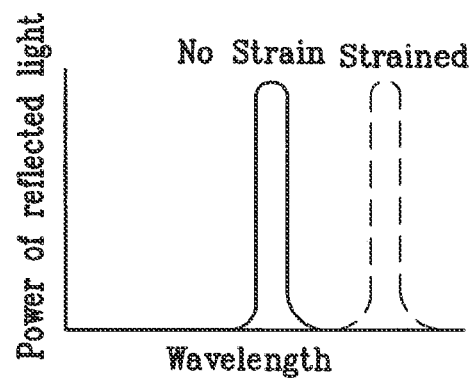
FIG. 12D illustrates shifting of the reflectance peak to longer wavelengths by the optical fiber sensor of FIGS. 12A-12C.

Optical sensors may be created by fixing an optical fiber 380 to the flexible substrate 300 such that it crosses the critical contact area over the coil pole treatment faces 22, 24. Multiple optical fibers may be used to isolate a particular location. Light from a remote light source 390 is provided into optical fiber 380 and directed toward a fiber Bragg grating 400 as illustrated in FIG. 12A. When the light makes contact with the fiber Bragg grating 400, the fiber(s) of the fiber Bragg grating 400 shown in cross-section in FIG. 12B deflect as illustrated in FIG. 12C so as to affect light transmission efficiency. For example, the reflectance peak may be shifted to longer wavelengths as shown in FIG. 12D, which is, in turn, detected by an optical detector (e.g. photodiode) 410 (FIG. 12A). Thus, the fiber Bragg grating 400 is attached to the flexible substrate 300 in such a way that deflection changes the amount of light reflected from the fiber Bragg grating 400. Light is reflected off of the flexible substrate 300 so that it vibrates when magnetically pulsed. The modulation of the light is measured. When vibration is minimal, contact is good. A thin liquid-filled bladder (e.g., bladder 310 of FIG. 11A) may be applied to the flexible substrate 300 and positioned such that contact at the critical areas of the coil pole treatment faces 22, 24 results in compression of the bladders 310 on both sides of the coil 360 which, in turn, displaces liquid to an optical detector 410 that detects the displacement. In accordance with the invention, the optical detector 410 may include a photodiode, a photo transistor, and the like.

Acoustic Sensors

Acoustic sensors may be mounted on the e-shield as in the embodiment of FIG. 11B so as to produce an acoustic sound when pulsed. This sound is reduced in magnitude and the frequency shifts when compressed against the head. The acoustic sensors detect the change in sound level. Any change is determined by processing circuitry 80 (FIG. 2) or signal processing software.

Figure 13A:
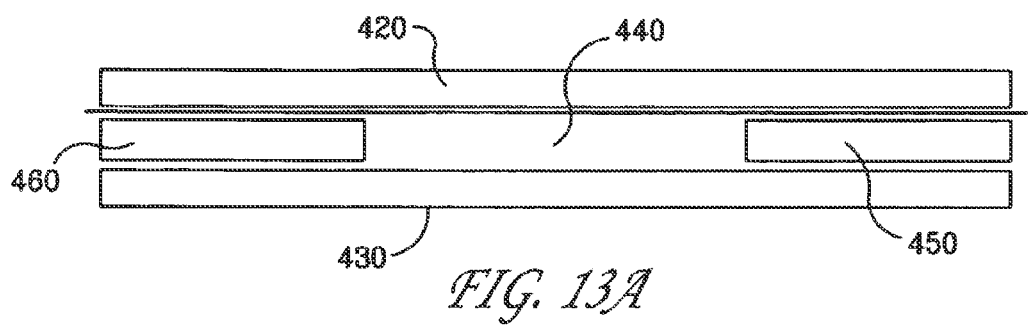
FIG. 13A illustrates a sample acoustic sensor embodiment in which flexible membranes in a non-contact position are separated by an acoustic channel that, in turn, connects an acoustic source to an acoustic transducer.
Figure 13B:
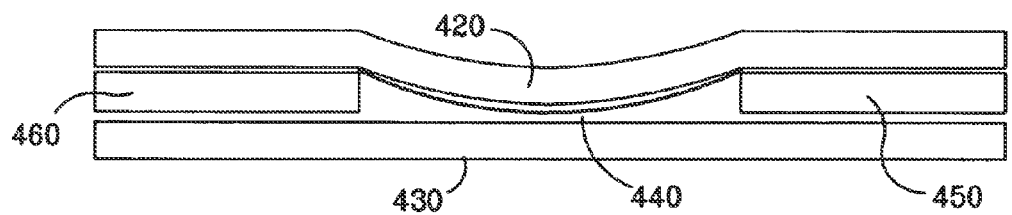
FIG. 13B illustrates that when the flexible membranes of FIG. 13A are pressed (against the head, for example), the acoustic channel is disrupted, thereby reducing the sound in magnitude and/or causing a frequency shift.

FIG. 13A illustrates a sample acoustic sensor embodiment in which flexible membranes 420, 430 in a non-contact position are separated by an acoustic channel 440 that, in turn, connects an acoustic source 450 to an acoustic transducer 460. As shown in FIG. 13B, when the flexible membranes 420, 430 are pressed (against the head, for example), the acoustic channel 440 is disrupted, thereby reducing the sound in magnitude and/or causing a frequency shift. Those skilled in the art will appreciate that the acoustic source 450 and acoustic transducer 460 may produce and detect sounds in the audible range and/or the ultrasonic range.

Figure 14A:
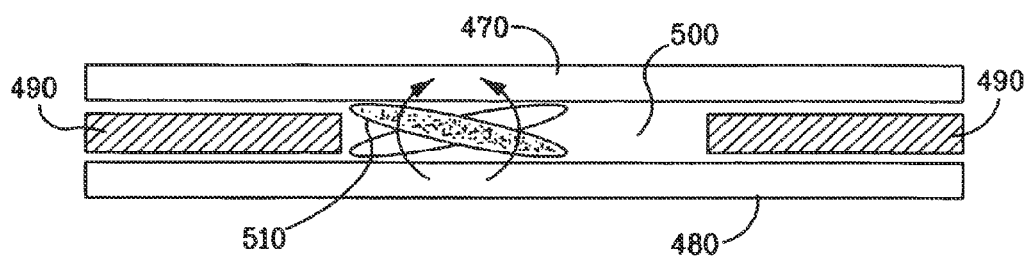
FIG. 14A illustrates an embodiment of a device including flexible membranes separated by spacers so as to define a cavity including a conductive disk that rattles within the cavity when the ambient magnetic field is pulsed.
Figure 14B:
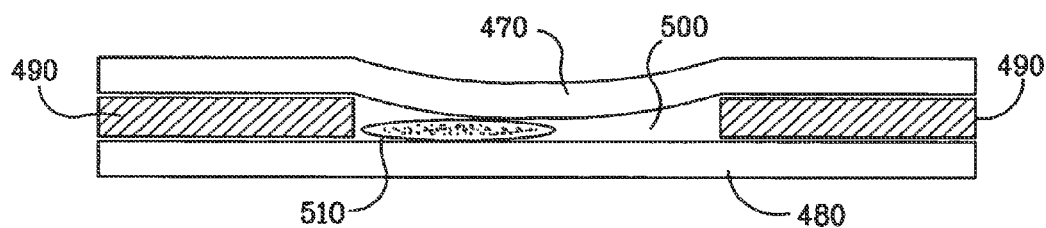
FIG. 14B illustrates immobilization of the conductive disk of FIG. 14A so as to significantly damp the rattling sound when the device is compressed against the patient.

Another type of acoustic sensor may be implemented as a device constructed on the substrate 350 (FIG. 11B) so as to intentionally "rattle" or makes an obvious audible sound when the TMS coil is pulsed and the substrate is not compressed against the patient's head. As illustrated in FIG. 14A, such a device includes flexible membranes 470, 480 that are separated by spacers 490 so as to define a cavity 500 between the flexible membranes 470, 480. The cavity includes a conductive disk 510 that experiences torque as indicated by the arrows so as to rattle within cavity 500 when the ambient magnetic field is pulsed. As illustrated in FIG. 14B, the device is designed to significantly damp the sound when compressed against the head. In this case, the flexible membranes 470, 480 immobilize the conductive disk 510 to prevent rattling within the cavity 500 when the flexible membranes 470, 480 are compressed (e.g., against the patient's head). The audible feedback (e.g., lack of rattling sound) is the indicator to the operator that the coil is in contact with the patient's head. Since the sound is audible, no acoustic sensors are necessary.

As illustrated in FIG. 15, an acoustic transducer 520 (audible or ultrasonic) may be mounted or attached to the patient's scalp at a position away from the magnetic field generated by the TMS coil assembly 20 so as to detect sound waves conducted through the skull that are generated by the TMS coil within the TMS coil assembly 20 when pulsed and mechanically coupled to the skull through contact with the patient's head. When the TMS coil assembly 20 is pulsed it generates an audible or inaudible vibration. When the TMS coil assembly 20 is in good contact with the skull, this sound is transmitted effectively to the skull which in turn is detected by acoustic transducer 520 applied to the patient's head at a convenient location (typically not directly beneath the coil). The output of the acoustic transducer 520 is applied to signal processing electronics (which may be in signal processing electronics 80) to detect a large change in the conducted sound has occurred, thereby indicating a disruption in the contact with the skull. The characteristics of the received sound wave varies (e.g., spectral shift or amplitude change) in accordance with the degree of mechanical coupling of the TMS coil assembly 20 with patient's skull. For example, low frequency waves are attenuated when the TMS coil assembly 20 is not in direct contact with the patient's skull, thereby changing the acoustic signature of the signal generated when the TMS coil is pulsed.

Inductive Coupling Sensors

Figure 16A:
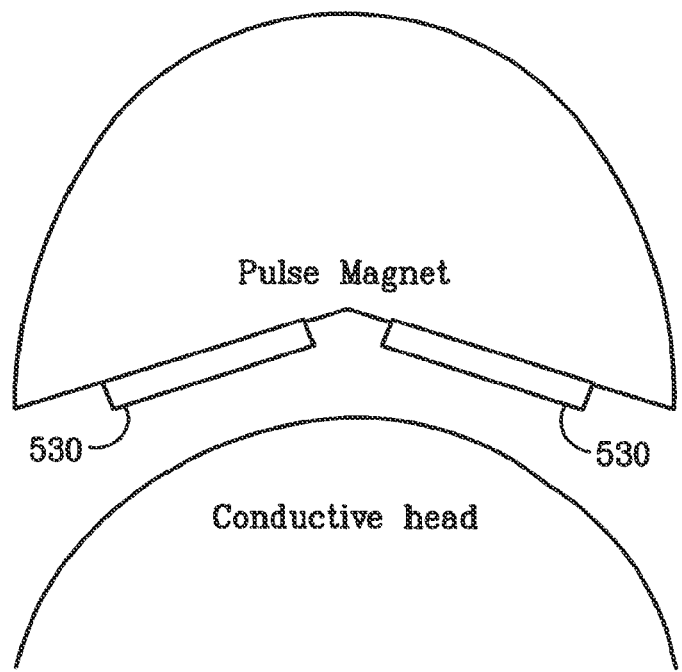
FIG. 16A illustrates a sensor embodiment implementing inductive coupling sensors whereby a tuned coil is mounted to the substrate of the TMS coil assembly.
Figure 16B:
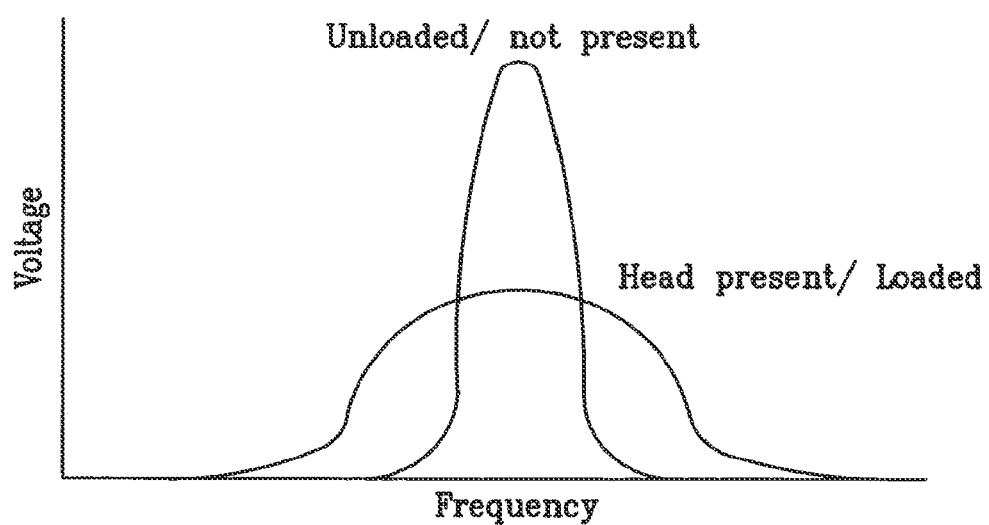
FIG. 16B illustrates tuned frequency shifts by the embodiment of FIG. 16A when the substrate and TMS coil assembly are in physical contact with the patient's head.

To implement inductive coupling sensors, a tuned coil 530 is mounted to substrate 60 as shown in FIG. 16A. The tuned frequency shifts as illustrated in FIG. 16B when the substrate 60 and TMS coil assembly 20 are in physical contact with the patient's head. Care must be taken to design the tuned circuit so that it is compatible with the pulsed magnetic field. The e-shield coils are pulsed independently from the TMS compensation pulse at a frequency that is sensitive to changes to coil loading (and corresponding changes in inductance). Changes in the coil current waveform are detected and discriminated as to whether the e-shield is located against the patient's head or not. Compressible tuned coil 530 is mounted on the substrate and is designed so that its shape (particularly its cross section with respect to the TMS field) is distorted when compressed against the patient's head. In other words, a different induced current will be produced by a frequency counter when the compressible tuned coil 530 is compressed as compared to the uncompressed state. This induced current is then detected by signal processing electronics in signal processing electronics 80.

Capacitive Coupling Sensors

As illustrated in FIG. 17, EEG-type leads and electrodes 540, or their equivalents, may be used to sense currents induced in the scalp by the TMS magnetic pulse. If the TMS coil assembly 20 is moved away from the scalp, these currents will shift and diminish in amplitude. This change is detected by processing the signals from the EEG-type leads 540 in suitable signal processing electronics. A minimum of two EEG-type leads is required. Those skilled in the art will appreciate that careful placement of the EEG-type electrodes 540 and appropriate filtering of the detected signal in the signal processing electronics is important in order to avoid artifacts due to patient movement or coupling with the TMS field.

Temperature Sensors

Figure 18:
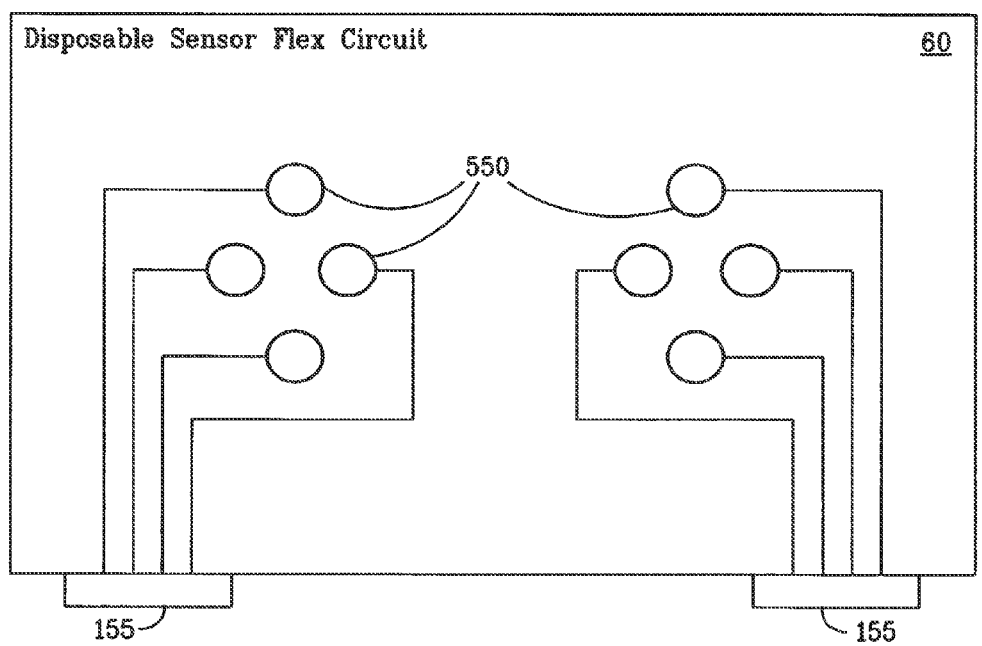
FIG. 18 illustrates an embodiment in which temperature sensors (e.g., thermistors, thermocouples) are applied near the two critical contact areas on the substrate and the outputs provided to processing circuitry for a determination of whether the detected temperatures track each other or if there is an abrupt temperature change indicating a change in contact of one or more of the sensors with the skull.

As illustrated in FIG. 18, temperature sensors (e.g., thermistors, thermocouples) 550 may be applied near the two critical contact areas 22, 24 on the substrate 60 and the outputs provided to processing circuitry (such as signal processing electronics 80) via connectors 155. Normally, the temperature of the two sides will track each other; however, if one or more of the temperature sensors 550 is not in contact with the patient's skull, there may be an unexpected abrupt temperature change indicating a change in contact of the sensor(s) 550 with the skull. In other words, if there is an unexpected significant change in the difference or ratio of the two temperatures (i.e., if the change is above a predetermined threshold), it is likely due to one side not being in contact with the patient's head. On the other hand, if the temperature detected by one or more temperature sensors 550 unexpectedly changes abruptly, then this alone could indicate that the temperature sensor(s) 550 is no longer in contact with the skull. This method has the disadvantage of a relatively slow response (i.e. several seconds). However, the unique advantage of this approach is the added feature of allowing the operator to optimize TMS protocol parameters while staying beneath safe temperature levels. It can also be used as a safety feature to detect failures in the TMS system that could produce excessive temperatures in the surfaces that contact the patient.

Those skilled in the art will appreciate that other sensing devices may be used to determine whether the TMS coil assembly is properly placed against the patient's head during treatment. Accordingly, any such modifications are intended to be included within the scope of this invention as defined by the following exemplary claims.

What is claimed:

1. A transcranial magnetic stimulation (TMS) system for providing TMS treatment to a patient, the TMS system comprising:
    a TMS coil assembly comprising a TMS coil;
    a pulse generating device configured to apply pulses to the TMS coil during TMS treatment of a patient;
    a sensor configured to identify locations of a plurality of contact areas on the TMS coil assembly that are in contact with the patient's head such that the contact areas on the TMS coil assembly are distinguishable from non-contact areas on the TMS coil assembly; and
    signal processing circuitry configured to process outputs of said sensor to provide an indication of whether said TMS coil assembly is properly disposed based on the locations of the contact areas on the TMS coil assembly that are in contact with the patient's head.

2. The TMS system as in claim 1, wherein said sensor comprises at least one sensor disposed in or on a flexible substrate placed between said TMS coil and a position at which pulses are applied.

3. The TMS system as in claim 2, wherein said at least one sensor comprises variable resistance sensors configured to output an output signal that is proportionate to applied contact pressure, whereby a change in resistance above a predetermined threshold is identified as an indication of contact.

4. The TMS system as in claim 3, wherein said variable resistance sensors have high impedances so as to minimize induced current therein.

5. The TMS system as in claim 2, wherein said at least one sensor comprises at least one fluid displacement sensor and fluid filled bladders connected by a non-compressible manifold to said at least one fluid displacement sensor such that compression of a bladder causes a change in pressure at the at least one fluid displacement sensor.

6. The TMS system as in claim 5, wherein said at least one fluid displacement sensor, said fluid filled bladders and said non-compressible manifold are disposed on an electrical shielding device disposed between the position and said TMS coil.

7. The TMS system as in claim 5, wherein said fluid filled bladders are disposed directly over respective pole faces of said TMS coil.

8. The TMS system as in claim 7, wherein said signal processing circuitry comprises artifact removal circuitry and a threshold detection device that indicates whether a predetermined force has been applied to at least one of said fluid filled bladders by a corresponding pole face of said TMS coil so as to indicate proper contact of said TMS coil to the position.

9. The TMS system as in claim 5, wherein fluid in said fluid filled bladders comprises a substantially non-electrically-conductive fluid.

10. The TMS system as in claim 2, wherein said at least one sensor comprises optical fibers that cross the position and an optical grating disposed on said substrate, whereby light passing through said optical fibers is deflected when contact is made by said TMS coil to said position so as to change an amount of light reflected by said optical grating, the reflected light being detected by an optical detector.

11. The TMS system as in claim 10, wherein said optical detector comprises one of a photodiode and a photo transistor.

12. The TMS system as in claim 2, wherein said at least one sensor comprises an acoustic sensor that detects sound waves generated when said TMS coil is pulsed by said pulse generating device and provides a detected signal to said signal processing circuitry for a determination as to whether the detected signal is indicative of said TMS coil being pressed against the patient.

13. The TMS system as in claim 2, further comprising an acoustic device that produces a sound when said TMS coil is pulsed by said pulse generating device and reduces an amplitude of said sound as the acoustic device is compressed by the TMS coil against the position and wherein said at least one sensor comprises at least one acoustic sensor that detects said sound and provides an amplitude signal to said signal processing circuitry for a determination as to whether an amplitude change has occurred.

14. The TMS system as in claim 1, wherein said at least one sensor comprises a conductive disk placed in a cavity bounded by flexible substrates, said conductive disk moving within the cavity when said flexible substrates are not compressed so as to cause an audible sound when said TMS coil is pulsed by said TMS pulse generating device.

15. The TMS system as in claim 14, wherein compression of said flexible substrates against the position substantially immobilizes the conductive disk so as to reduce or eliminate said audible sound.

16. The TMS system as in claim 2, wherein said at least one sensor comprises inductive coupling sensors comprising at least one tuned coil mounted on said substrate, wherein a tuned frequency of said at least one tuned coil shifts when said TMS coil is in physical contact with the position.

17. The TMS system as in claim 16, wherein a shape of said at least one tuned coil is distorted when compressed against the position by said TMS coil, and a resulting induced current in said tuned coil is detected by said signal processing circuitry to provide said indication of whether said TMS coil assembly is properly disposed with respect to the position during application of pulses to said TMS coil.

18. The TMS system as in claim 2, wherein said at least one sensor comprises EEG leads that sense currents induced in the position by a TMS pulse from said TMS coil.

19. The TMS system as in claim 18, wherein said signal processing circuitry compares amplitudes of sensed currents to a threshold as said indication of whether said TMS coil assembly is properly disposed with respect to the position during application of pulses to said TMS coil.

20. The TMS system as in claim 2, wherein said at least one sensor comprises at least one temperature sensor.

21. The TMS system as in claim 20, wherein said signal processing circuitry processes outputs of said temperature sensors to determine if a temperature difference between respective temperature sensors is above a predetermined threshold.

22. The TMS system as in claim 1, wherein the sensor comprises a loop of conducting material placed at a position at which pulses are to be applied to the TMS coil, the loop of conducting material having an induced voltage therein when pulses are applied by the pulse generating device to the TMS coil when the TMS coil is in proximity to the loop of conducting material, and wherein whether the induced voltage exceeds a predetermined threshold serves as an indication of whether the TMS coil is properly disposed.

23. A device that detects the proximity of a transcranial magnetic stimulation (TMS) coil assembly to an anatomy of a patient during TMS treatment, the TMS coil assembly comprising a TMS coil, the device comprising:
   at least one sensor disposed between said TMS coil and said anatomy so as to identify locations of a plurality of contact areas on the TMS coil assembly that are in contact with the patient's head such that the contact areas on the TMS coil assembly are distinguishable from non-contact areas on the TMS coil assembly; and
   processing circuitry configured to process outputs of said at least one sensor for determining whether said TMS coil assembly is properly disposed based on the locations of the contact areas on the TMS coil assembly that are in contact with the patient's head.

24. The device as in claim 23, wherein said at least one sensor comprises variable resistance sensors configured to provide an output signal that is proportionate to applied contact pressure, whereby a change in resistance above a predetermined threshold is identified as an indication of contact.

25. The device as in claim 24, wherein said variable resistance sensors have high impedances so as to minimize induced current therein.

26. The device as in claim 23, wherein said at least one sensor comprises at least one fluid displacement sensor and fluid filled bladders connected by a non-compressible manifold to said at least one fluid displacement sensor such that compression of a bladder causes a change in pressure at the at least one fluid displacement sensor.

27. The device as in claim 26, wherein said at least one fluid displacement sensor, said fluid filled bladders and said non-compressible manifold are disposed on an electrical shielding device that shares a flexible substrate.

28. The device as in claim 26, wherein fluid filled bladders are disposed directly over respective pole faces of said TMS coil during TMS treatment.

29. The device as in claim 26, wherein fluid in said fluid filled bladders comprises a substantially non-electrically-conductive fluid.

30. The device as in claim 23, wherein said at least one sensor comprises optical fibers that cross a position at which a pulse generating device is configured to apply pulses to the TMS coil and an optical grating disposed on a substrate, whereby light passing through said optical fibers is deflected when contact is made by said TMS coil to said position so as to change an amount of light reflected by said optical grating, the reflected light being detected by an optical detector.

31. The device as in claim 30, wherein said optical detector comprises one of a photodiode and a photo transistor.

32. The device as in claim 23, wherein said at least one sensor comprises an acoustic sensor that detects sound waves generated when said TMS coil is pulsed by a pulse generating device and provides a detected signal to signal processing circuitry for a determination as to whether the detected signal is indicative of said TMS coil being pressed against the patient.

33. The device as in claim 23, further comprising an acoustic device that produces a sound when said TMS coil is pulsed by a pulse generating device and reduces an amplitude of said sound as the acoustic device is compressed by the TMS coil against a position at which the pulse generating device is configured to apply pulses to the TMS coil and wherein said at least one sensor comprises at least one acoustic sensor that detects said sound and provides an amplitude signal to signal processing circuitry for a determination as to whether an amplitude change has occurred.

34. The device as in claim 23, wherein said at least one sensor comprises a conductive disk placed in a cavity bounded by flexible substrates, said conductive disk moving within the cavity when the flexible substrates are not compressed so as to cause an audible sound when said TMS coil is pulsed by a pulse generating device.

35. The device as in claim 34, wherein compression of said flexible substrates against a position at which the pulse generating device is configured to apply pulses to the TMS coil substantially immobilizes the conductive disk so as to reduce or eliminate said audible sound.

36. The device as in claim 23, wherein said at least one sensor comprises inductive coupling sensors comprising at least one tuned coil mounted on a substrate, wherein a tuned frequency of said at least one tuned coil shifts when said TMS coil is in physical contact with a position at which a pulse generating device is configured to apply pulses to the TMS coil.

37. The device as in claim 36, wherein a shape of said at least one tuned coil is distorted when compressed against the position by said TMS coil, and a resulting induced current in said at least one tuned coil is output as an indication of whether said TMS coil is properly disposed with respect to the position during TMS treatment.

38. The device as in claim 23, wherein said at least one sensor comprises EEG leads that sense currents induced in a position at which a pulse generating device is configured to apply pulses to the TMS coil by a TMS pulse from said TMS coil.

39. The device as in claim 23, wherein said at least one sensor comprises temperature sensors.

40. The device as in claim 23, wherein said at least one sensor comprises a loop of conducting material placed at a position at which a pulse generating device is configured to apply pulses to the TMS coil under said TMS coil, said loop of conducting material having an induced voltage therein when pulses are applied to said TMS coil when said TMS coil is in proximity to said loop of conducting material.

41. A method of providing transcranial magnetic stimulation (TMS) treatment to a patient, comprising the steps of:
    identifying locations of a plurality of contact areas on a TMS coil assembly that are in contact with the patient's head;
    identifying locations of a plurality of non-contact areas on the TMS coil assembly that are not in contact with the patient; and
    providing an indication of whether the TMS coil assembly is properly positioned based on the locations of the contact areas on the TMS coil assembly that are in contact with the patient's head.

42. The method of claim 41, wherein the TMS coil assembly comprising a TMS coil, the method further comprising determining whether the TMS coil assembly is properly positioned by comparing the locations to a position at which pulses are to be applied to the TMS coil during TMS treatment of the patient.

43. The method as in claim 41, wherein the TMS coil assembly comprises a TMS coil, the method further comprising:
    disposing a sensor between said TMS coil and the patient's head; and
    applying pulses to the TMS coil during TMS treatment of the patient.

44. The method of claim 41, further comprising:
    disposing a loop of conducting material at a position at which pulses are to be applied to a TMS coil during TMS treatment of a patient, said loop of conducting material having an induced voltage therein when pulses are applied to said TMS coil when said TMS coil is in proximity to said loop of conducting material;
    applying pulses to said TMS coil during TMS treatment of the patient;
    measuring said induced voltage; and
    determining whether said induced voltage exceeds a predetermined threshold for indicating whether said TMS coil is properly disposed during application of pulses to said TMS coil.

* * * * *